United States Patent [19]
Counsell et al.

[11] Patent Number: 5,851,510
[45] Date of Patent: Dec. 22, 1998

[54] HEPATOCYTE-SELECTIVE OIL-IN-WATER EMULSION

[75] Inventors: Raymond E. Counsell; Marc A. Longino; Jamey P. Weichert; Douglas A. Bakan, all of Ann Arbor, Mich.

[73] Assignee: The Board of Regents of The University of Michigan, Ann Arbor, Mich.

[21] Appl. No.: 243,596

[22] Filed: May 16, 1994

[51] Int. Cl.$^6$ .............................. A61K 49/00; B01J 13/00
[52] U.S. Cl. ........................ 424/9.45; 252/312; 252/314; 424/1.89; 424/9.37; 424/9.4; 514/744; 514/938; 514/941
[58] Field of Search ............................. 252/312; 436/24; 514/938, 941; 424/9.37, 9.4, 9.45

[56] References Cited

U.S. PATENT DOCUMENTS

| | | | |
|---|---|---|---|
| Re. 32,393 | 4/1987 | Wretlind et al. | 514/219 |
| 3,992,513 | 11/1976 | Petkau et al. | 424/1.37 |
| 4,073,943 | 2/1978 | Wretlind et al. | 514/772 |
| 4,309,289 | 1/1982 | Head | 210/649 |
| 4,816,247 | 3/1989 | Desai et al. | 514/938 X |
| 4,873,075 | 10/1989 | Counsell et al. | 424/1.1 |
| 4,917,880 | 4/1990 | Wretlind et al. | 424/5 |
| 4,957,729 | 9/1990 | Counsell et al. | 424/5 |
| 4,970,209 | 11/1990 | Wretlind et al. | 514/221 |
| 5,004,756 | 4/1991 | Ogawa et al. | 514/655 |
| 5,039,527 | 8/1991 | Tabibi | 424/450 |
| 5,055,303 | 10/1991 | Riley, Jr. | 424/436 |
| 5,080,885 | 1/1992 | Long, Jr. | 424/9.4 |
| 5,093,042 | 3/1992 | Counsell et al. | 554/106 |
| 5,093,044 | 3/1992 | Wretlind et al. | 514/547 |
| 5,098,606 | 3/1992 | Nakajima et al. | 514/938 X |
| 5,116,599 | 5/1992 | Rogers, Jr., et al. | 424/9 |
| 5,152,923 | 10/1992 | Weder et al. | 252/312 |
| 5,171,737 | 12/1992 | Weiner et al. | 514/3 |
| 5,234,680 | 8/1993 | Rogers et al. | 424/9 |
| 5,445,811 | 8/1995 | Norrlind et al. | 424/9.4 |

FOREIGN PATENT DOCUMENTS

| | | |
|---|---|---|
| 0 132 027 A1 | 1/1985 | European Pat. Off. . |
| WO 87/01035 | 2/1987 | WIPO . |
| WO 89/05638 | 6/1989 | WIPO . |
| 0 315 079 A1 | 10/1989 | WIPO . |
| WO 92/04886 | 4/1992 | WIPO . |
| WO 92/07551 | 5/1992 | WIPO . |
| WO 92/13555 | 8/1992 | WIPO . |
| WO 92/15283 | 9/1992 | WIPO . |
| WO 92/17162 | 10/1992 | WIPO . |
| WO 92/18169 | 10/1992 | WIPO . |
| WO 92/21384 | 12/1992 | WIPO . |
| WO 94/08626 | 4/1997 | WIPO . |

OTHER PUBLICATIONS

Clark, et al., "Phosphatidylcholine Composition of Emulsions Influences Triacylglycerol Lipolysis and Clearance from Plasma," *Biochimica et Biophysica Acta*, vol. 920, pp. 37–46 (1987).

Cooper, et al., "Rates of Removal and Degradation of Chylomicron Remnants by Isolated Perfused Rat Liver," *J. Lipid Research*, vol. 19, pp. 635–643 (1978).

Cooper, "Hepatic Clearance of Plasma Chylomicron Remnants," vol. 12, No. 4, pp. 386–396 (1992).

Counsell et al., "Lipoproteins as Potential Site–Specific Delivery Systems for Diagnostic and Therapeutic Agents," *J. Med. Chem.*, vol. 25, No. 10, pp. (1982).

Damle et al., "Potential Tumor–or organ–imaging Agents XXIV: Chylomicron Remnants as Carrier for Hepatographic Agents," *J. Pharm. Science.*, vol. 72, No. 8, pp. 898–901 (1983).

Gardner et al., "Comparison of the Metabolism of Chylomicrons and Chylomicron Remnants by the Perfused Liver," *Biochem. J.*, vol. 170, pp. 47–55 (1978).

Grimes, "Formulation and Evaluation of Ethiodized Oil Emulsion for Intravenous Hepatography," *J. Pharm. Sci.*, vol. 68, No. 1, pp. 52–56 (1979).

"Handbook of Chemistry and Physics," 58th edition, CRC Press, B–303–B–305 (1977–1978).

Hamilton et al., "Apolipoprotein E Localization in Rat Hepatocytes by immunogold Labeling of Cryothin Sections," *J. Lipid Research*, vol. 31, pp. 1589–1603 (1990).

Ivancev et al., "Effect of Intravenously Injected Iodinate Lipid Emulsions on the Liver," *Acta Radiologica*, vol. 30, Fasc. 3, pp. 291–297 (1989).

Ivancev et al., "Experimental Investigation of a New Iodinated Lipid Emulsion for Computed Toography of the Liver," *Acta Radiologica*, vol. 30, Fasc. 4, pp. 407–412 (1989).

Ivancev et al., "Clinical Trials With a New Iodinated Lipid Emulsion for Computed Tomography of the Liver," *Acta Radiologica*, vol. 30, Fasc. 5, pp. 449–457, Sep.–Oct. 1989.

(List continued on next page.)

Primary Examiner—Richard D. Lovering
Attorney, Agent, or Firm—Rohm & Monsanto, PLC

[57] ABSTRACT

A heat and shelf-stable oil-in-water emulsion useful as a tissue or cell-selective delivery vehicle. Radioactive or stable, synthetic or semi-synthetic polyhalogenated triglycerides, such as 2-oleoylglycerol-1,3-bis[7-(3-amino-2,4,6-triiodophenyl)heptanoate] or 2-oleoylglycerol-1,3-bis[ω-(3,5-bis-trifluoromethyl)heptanoate] or phenyl acetate, can be incorporated into the lipophilic core of a lipoprotein-like emulsion particle. The lipophilic core is surrounded by a phospholipid membrane comprising cholesterol and apolipoproteins. For hepatocyte-selective delivery, the emulsion is chylomicron remnant-like by being in a size range of 50 to 200 nm as measured by number weighting analysis with a narrow size distribution (<2% greater than 300 nm) and having a composition simulating naturally-occurring chylomicron remnants. Use of cholesterol in the emulsion formula facilitates association of apolipoproteins, especially Apo E which are recognized by liver cells and necessary for binding and uptake. Stability and size constraints can be achieved by using ultra high energy mixing equipment, such as such as the MicroFluidizer (Microfluidics Corp., Newton, Mass.) to form the emulsion. In preferred embodiments, osmolality of the emulsion is controlled by glycerol rather than normal saline.

18 Claims, 13 Drawing Sheets

OTHER PUBLICATIONS

Jones et al., "Uptake and Processing of Remnants of Chylomicrons and Very Low Density lipoproteins by Rat Liver," *J. Lipid Res.*, vol. 25, pp. 1151–1158 (1984).

Kowal, et al., "Low Density Lipoprotein Receptor–related Protein Mediates Uptake of Cholesteryl Esters Derived from Apoprotein E–enriched Lipoproteins," *Biochemistry*, vol. 86, pp. 5810–5814 (1989).

Lange, et al., "Esophageal Anastomotic Leaks: Preliminary results of Treatment with Balloon Dilation," *Radiology*, vol. 165, pp. 45–47 (1987).

Longino, et al., "Importance of Emulsification Method on the Particle Size of Fluorotriglyceride Microemulsions for Hepatic $^{19}$F–MR Imaging," Book of Abstracts, vol. 2, *Soc. of Magnetic Resonance*, p. 820 (1989).

Longino, et al., Abstract, Association of University Radiologists, vol. 9(1):53 (1990).

Longino, et al., Abstract 8–7, *Investigative Radiology*, vol. 25, No. 12, p. 1357 (1990).

Nagata, et al., "Role of Low Density Lipoprotein Receptor–dependent and –Independent Sites in Binding and Uptake of Chylomicron Remnants in Rat Liver," *J. Biol. Chem.*, vol. 263, No. 29, pp. 15151–15158 (1988).

Nilsson–Ehle and Schotz, "A Stable, Radioactive Substrate Emulsion for Assay of Lipoprotein Lipase," *J. of Lipid Research*, vol. 17, p. 536 (1976).

Pattniak, et al., "Effect of Size and Competition by Lipoproteins and Apolipoproteins on the Uptake of Chylomicrons and Chylomicron Remnants by Hepatoma Cells in Culture," *Biochimica et Biophysica Acta*, vol. 617, pp. 335–346 (1980).

Redgrave, et al., "Cholesterol is Necessary for Triacylglycerol–phospholipid Emulsions to Mimic the Metabolism of Lipoproteins," *Biochimica et Biophysica Acta*, vol. 921, pp. 154–157 (1987).

Redgrave, et al., "The Effect of Triacyl–sn–glycerol Structure on the Metabolism of Chylomicrons and Triacylglycerol–rich Emulsion in the Rat," *J. Biol. Chem.*, vol. 263, pp. 5115–5123 (1988).

Schumacher, et al., "Experimental Data on the Problem of Specific Hepatosplenography with Radiodense Lipomicrons," *Europ. J. Radiol.*, vol. 5, pp. 167–174 (1985).

Schwendner, et al., "Potential Organ or Tumor Imaging Agents. 32. A Triglyceride Ester of ρ–Iodophenyl Pentadecanoic Acid as a Potential Hepatic Imaging Agent," *Nucl. Med. Biol.*, vol. 19, No. 6, pp. 639–650 (1992).

Sherrill et al., "Characterization of the Sinusoidal Transport Process Responsible for Uptake of Chylomicron by the Liver," *J. Biol. Chem.*, vol. 253, No. 6, pp. 1859–1867 (1978).

Stryer, *Biochemistry*, 2d Ed., pp. 213–214 and 470–471 (1981).

Sultan, et al., "Inhibition of Hepatic Lipase Activity Impairs Chylomicron Remnant–removal in Rats," *Biochimica et Biophysica Acta*, vol. 1042, pp. 150–152 (1990).

Vermess, et al., Development and Experimental Evaluation of a Contrast Medium for Computed Tomographic Examination of the Liver and Spleen, *J. Computer Assisted Tomography*, vol. 31, No. 1, pp. 25–31 (1979).

Washington and Davis, The Production of Parenteral Feeding Emulsions by Microfluidizer, *Int'l. J. Pharm.*, vol. 44, pp. 169–176 (1988).

Weichert, et al., *J. Med. Chem.*, vol. 29, pp. 1674 and 2457 (1986).

Weichert, et al., Abstract of 7th Annual SMRM, vol. 1, p. 484 (Aug. 22–26 1988).

HEPATOCYTE-SELECTIVE OIL-IN-WATER EMULSION

STATEMENT OF GOVERNMENT RIGHTS

This invention was made with government support under Grant No. CA08349 by the National Institutes of Health. The government has certain rights in the invention.

BACKGROUND OF THE INVENTION

This invention relates generally to an oil-in-water emulsion, and more particularly, to an oil-in-water emulsion which functions as a tissue-specific delivery vehicle for lipophilic or amphipathic diagnostic, therapeutic, or other bioactive or inactive agents incorporated therein.

Imaging agents are used for diagnostic modalities, such as computed tomography (CT), magnetic resonance (MR), ultrasound or nuclear medicine, to enhance the image contrast between tissue types. It is a shortcoming in the present state of the art that most of the currently used imaging agents are limited in action to the vascular and/or extracellular compartments. Thus, every tissue that receives a normal blood supply will also receive the diagnostic agent. Tissue-specific image enhancement is therefore compromised. Non-specific agents which reside in the extracellular space are useful primarily to discriminate anatomical features of tissues and structures. However, an imaging agent, which can deliver a diagnostic agent to the intracellular environment of a targeted tissue, could provide a means of assessing the metabolic and/or biochemical activity of the targeted tissue in addition to providing the standard anatomical visualization achieved with extracellular imaging agents.

In addition to the foregoing, agents which localize in the extracellular spaces are cleared very rapidly from the body. Due to imaging hardware limitations, a predetermined minimum period of time is required to collect the data that are used to form a diagnostic image. Consequently, a contrast agent that clears too quickly from the body must be administered in a very large dose in order to maintain a concentration gradient sufficient to achieve an acceptable quality of the image. Thus, the administration of many currently available diagnostic imaging agents is a complicated process balancing the benefits of image enhancement against the dangers of injecting large volumes of material into a living being in a short period of time. In the case of CT imaging, diagnostic imaging agents are commonly administered to the patient in volumes as large as 150 to 250 ml at rates of 1.5 to 2.5 ml/sec. Injection of currently available agents at this rate can induce nausea, headaches, convulsions and other undesirable and dangerous side effects. There is thus a need for a tissue-specific delivery vehicle that concentrates the imaging agent in a single targeted organ or tissue type and thus permits slower, controlled injection of a substantially smaller dose. Of course, a lower dose would also minimize the potential for toxicity and side effects, as well as preclude the need for expensive power injectors.

For therapeutic purposes, such as the delivery of radioactive therapeutic agents, it would be advantageous to target specific tissue and reduce the destructive effects of the radioactive agents on surrounding tissue. There has been much discussion of gene therapy for treatment of such diseases as familial hypercholesterolemia, hepatitis, or hepatomas. However, the delivery of corrective genetic material to abnormal tissues frequently fails because of an inability to target the genetic material to a specific tissue or to do so in sufficient quantities to replace the abnormal form of the gene. There is, therefore, a need in the art for a delivery vehicle which is capable of delivering genetic material to tissues at levels suitable for gene therapy.

Some known strategies for achieving tissue-specific delivery include the use of vehicles such as liposomes, antibody-linked conjugates and carbohydrate derivatives of the targeting compound. However, many of these known vehicles cannot form acceptable complexes with the moiety to be delivered or fail to accumulate the complexed moiety in the target tissue in quantities sufficient to be effective for imaging and/or therapy.

One of the most accurate, non-invasive radiologic examination techniques available for detection of hepatic masses is CT using water soluble, urographic contrast agents. However, the contrast agents commonly used in this well-known technique suffer from the typical limitations which plague other known contrast agents, including, for example, the requirement that large doses be administered, a nonspecific biodistribution, and an extremely short (<2 min.) residence time in the liver. As a result, CT has not been consistently successful at detecting lesions smaller than about 2 cm in diameter. These significant limitations of the known agents preclude early detection and therapy of cancer, since many metastases are smaller than the detection limits of the technique.

The inability of water-soluble urographic agents to detect lesions less than 2 cm in diameter with acceptable consistency may be due, in part, to the rapid diffusion of these agents out of the vasculature into interstitial spaces resulting in a rapid loss of contrast differential between normal liver tissue and tumors. There is, therefore, a need for a diagnostic contrast agent, or vehicle therefor, which delivers agent to the intracellular space of specific targeted tissue, such as liver tissue, so as to enhance the degree of selective visualization and further improve the detection limits of CT. A number of alternatives to water-soluble contrast agents have been investigated as potential liver CT contrast agents including, for example, radiopaque liposomes, iodinated starch particles, perfluoroctylbromide, iodipamide ethyl esters, and ethiodized oil emulsion (EOE-13). All of these agents are particulate in nature and of such a size for which liver specificity is mediated primarily via sequestration by the reticuloendothelial system (RES).

Liposomes, which are artificially prepared lipid vesicles formed by single or multiple lipid bilayers enclosing aqueous compartments are particulate in nature, and hence, have potential for delivering agents contained therein to the RES. Investigators have attempted to load liposomes with both ionic and non-ionic water-soluble urographic or hepatobiliary contrast agents, or to incorporate brominated phosphatidylcholine into the bilayer membrane. However, stabilization of the resulting liposome against loss of contrast media from the bilayers has proven to be a major problem. Moreover, incorporation of neutral lipophilic agents into the bilayer is limited by the low solubility of the lipophilic agents in the membrane matrix and the restricted loading capacity of the liposome.

Several monobrominated perfluorocarbons have been evaluated as contrast agents in animals. The most common of these, perfluoroctylbromide, has been shown to concentrate in the reticuloendothelial cells of the liver, spleen and other organs. The long residency times (weeks to months) and the large doses (5–10 g/kg) necessary for suitable opacification will most likely preclude the use of monobrominated perfluorocarbons in humans for diagnostic imaging purposes unless a means of specifically delivering small doses to a targeted organ is developed.

The most promising of the investigational agents mentioned above, EOE-13, has been extensively studied in both animals and humans in the United States. EOE-13, an emulsion of iodinated poppy seed oil (37% iodine by weight) in saline, offered considerable improvement in the detection of space-occupying lesions in the liver and spleen as compared to conventional water-soluble urographic agents. Despite acceptable clinical diagnostic efficacy, a high incidence of adverse reactions, including fever, chills, thrombocytopenia, hypotension, and respiratory distress, was reported. Moreover, additional problems were encountered in the sterilization of the EOE-13 preparation. These problems led to the discontinuation of the use of EOE-13 in humans.

Recently, investigators have demonstrated a direct relationship between emulsion particle size and macrophage involvement. The investigators tested three iodinated lipid emulsions, including EOE-13, having mean particle diameters ranging from 400–2000 nm. They observed a marked swelling of Kupffer cells which, when coupled with sinusoidal endothelial damage, resulted in sinusoidal congestion. Sinusoidal congestion often activates macrophages, resulting in the release of toxic mediators which may be responsible, in part, for the adverse reactions seen with these relatively large-sized particulate preparations. As a result, the investigators emulsified iodinated ethyl esters of fatty acids derived from poppyseed oil (Lipiodol-UF, Laboratoire Guerbet, France) with egg yolk phospholipids, in order to provide a preparation of smaller, more uniform particle size, called Intraiodol (not commercially available; see, for example, *Acta Radioloica,* Vol. 30, pages 407–412 and 449–457, 1989). Intraiodol has a particle size range of 110 to 650 nm (distribution mean diameter 310 nm). Initial results obtained with Intraiodol in animals and humans demonstrated a significant reduction in adverse reactions relative to those observed with EOE-13. However, Intraiodol continues to suffer from many disadvantages common in the prior art, including failure to achieve true specificity due to, inter alia, liposome (particulate) contamination which results in delivery to the RES, size and composition, and inability to achieve shelf and heat stability. Moreover, the iodine necessary for CT opacification is attached in an aliphatic linkage, which is well known to exhibit diminished in vivo stability.

Although Intraiodol, and other similar oil-in-water emulsions, have been called "chylomicron remnant-like" and "hepatocyte specific," these agents locate significantly in the spleen, which does not contain hepatocytes. A true hepatocyte-specific contrast agent will not locate substantially in the spleen and other RES associated organs unless there is saturation of the initial receptor-mediated process so that there is a shift in delivery to the cells of the RES. Further, a true hepatocyte-specific agent will be cleared primarily through the biliary system. None of the aforementioned emulsions demonstrate hepatocyte-specificity with biliary clearance studies.

Accordingly, there remains a great need in the art for target-specific delivery vehicles or compositions, including contrast-producing oil-in-water emulsions, for delivery of diagnostic, therapeutic, and other biologically active or inactive agents.

It is, therefore, an object of this invention to provide an improved delivery vehicle, specifically a target-selective oil-in-water emulsion for delivery of lipophilic agents, or lipophilic derivatives of water soluble agents, such as contrast agents, to the intracellular spaces of the targeted tissue.

It is another object of this invention to provide a target-specific delivery vehicle, specifically a hepatocyte-selective oil-in-water emulsion, which is chylomicron remnant-like with respect to size and biodistribution characteristics.

It is also an object of this invention to provide a target-selective oil-in-water emulsion which is shelf stable and heat stable so that it can be heat sterilized.

It is a further object of this invention to provide a method of preparing a target-selective oil-in-water emulsion which is chylomicron remnant-like, shelf and heat stable, and substantially free of liposome contamination.

SUMMARY OF THE INVENTION

The foregoing and other objects are achieved by this invention which is a synthetic oil-in-water lipid emulsion resembling endogenous lipoproteins in order to take advantage of the natural lipid transport system of a living being. The oil-in-water emulsion of the present invention is useful as a target-selective delivery vehicle. In specific embodiments, the oil-in-water emulsion simulates chylomicron remnants so that lipophilic or amphipathic compounds inserted into either the lipid core or the surrounding monolayer of the emulsion are delivered selectively to the hepatocytes via a receptor-mediated pathway. As used herein the term "receptor-mediated" means that metabolism of the oil-in-water emulsions of the present invention mimics the uptake and clearance of natural chylomicron remnants.

To summarize briefly the natural lipid transport system, lipids are transported in the plasma mainly in the form of free fatty acids, triglycerides, and cholesteryl esters. Free fatty acids are transported as a complex with plasma albumin, whereas triglycerides and cholesteryl esters are transported in the lipophilic core of plasma lipoproteins. The surface of plasma lipoproteins comprises a monolayer of phospholipid, cholesterol, and specific proteins known as apolipoproteins which regulate the entry and exit of particular lipids at specific targets. Cholesterol and triglycerides from dietary sources are absorbed by the intestinal tract and incorporated into chylomicrons which are subsequently secreted into and transported through the thoracic duct until they reach the circulation. Once in circulation, there is a rapid transfer of apoprotein C-II from circulating high density lipoproteins to the chylomicrons. Once associated with apoprotein C-II, the chylomicrons are acted upon by lipoprotein lipase in the capillary beds of several peripheral tissues including adipose, muscle (skeletal and heart), and lung. Lipoprotein lipase hydrolyzes much of the core triglyceride to glycerol and free fatty acids, most of which are taken up by the tissues for storage or oxidation. The remaining triglyceride-depleted chylomicrons, called chylomicron remnants, now contain lesser amounts of triglycerides, with cholesteryl esters as the main lipid component and apoprotein B (Apo B) and apoprotein E (Apo E) as the major apoprotein components. Chylomicron remnants are cleared very rapidly from the circulation by the liver via a receptor-mediated process that recognizes Apo B and Apo E. While lipoprotein lipase is the enzyme responsible for the hydrolysis of plasma triglycerides in extrahepatic tissues, hepatic triglyceride lipase is implicated in hepatic triglyceride hydrolysis and remnant uptake by hepatocytes. Hepatic clearance of chylomicron remnants from the circulation occurs mainly via the hepatocytes (parenchymal cells) rather than Kupffer cells (nonparenchymal cells).

Therefore, the synthetic oil-in-water emulsion of the present invention is designed to associate with plasma apoproteins such as Apo B and Apo E so as to be "hepatocyte-selective." The oil-in-water emulsion of the present invention is termed "hepatocyte-selective" in comparison to "hepatocyte-specific" emulsions as that term is used in the prior art, without definition.

In order to achieve Apo E association, however, the oil phase particles must have the correct size and composition, and must retain the correct size after sterilization and/or over the period of its shelf life. In accordance with the present invention, the mean oil phase particle size is between 50 and 200 nm (number weighted), with a narrow size distribution (50 to 300 nm) wherein no more than 2% of the particles have a diameter that falls outside of the range (i.e., being greater than 300 nm). The emulsion should have no detectable particles with a diameter greater than 1 μm. Moreover, the emulsion should not be contaminated with liposomes.

In addition, the composition must contain a sterol, which is preferably cholesterol, in an amount of up to 5% by weight in order to stabilize the emulsion and facilitate its association with Apo E, and preferably in the range of 0.4 to 0.5% (w/v) for hepatocyte-selective delivery of iodinated triglycerides. In accordance with preferred embodiments of the invention, the molar ratio of cholesterol to emulsifier, which may be a natural, synthetic, or semi-synthetic phospholipid, has been found to directly affect the particle diameter and dimensional stability. The preferred molar ratio of cholesterol to phospholipid for achieving an emulsion which successfully mimics chylomicron remnants is in the range of 0.05 to 0.70, and more specifically at 0.40 for hepatocyte-selective delivery of iodinated triglycerides.

"Hepatocyte-selectivity" as the term is used herein can be demonstrated by a liver to spleen uptake ratio of >4:1 at 30 minutes after injection based on % dose/organ values (see, Example 3 Table 2 below) and biliary clearance and elimination profiles (see, FIGS. 11 and 13–16). Based on the entire body of scientific literature describing the anatomical features of the hepatocytes and the surrounding sinusoidal spaces, particles with a diameter greater than approximately 300 nm are unable to access the surface of the hepatocytes. A hepatocyte-selective vehicle primarily delivers compound intracellularly to the targeted tissue and does not significantly deliver compound nonspecifically to the surface of the cells (extracellular) or to the sinusoids between the cells (see, FIGS. 17 and 18).

In a composition aspect of the invention, the synthetic heat stable hepatocyte-selective oil-in-water emulsion of the present invention has the general formula:

1. up to 50%(w/v) lipophilic core components;
2. up to 10% emulsifier (w/v);
3. up to 5% cholesterol (w/v);
4. up to 5% osmolarity adjusting agent (w/v);
5. optionally, up to 5% antioxidant (w/v); and
6. sterile, distilled water to final volume.

The types of agents which can be delivered to the hepatocytes by incorporation into the lipophilic core of the synthetic oil-in-water emulsions of the present invention are lipophilic and/or amphipathic compounds, which may be bioactive or bioinactive. The lipophilic core components comprise up to 50% (w/v) of the emulsion, and preferably between about 10% and 30% (w/v). The lipophilic core may comprise any pharmaceutically acceptable fat or oil of natural, synthetic, or semi-synthetic origin which is a pharmacologically inert nonpolar lipid that will locate in the lipophilic core of the oil-in-water emulsion. Specific examples include, without limitation, triglycerides, illustratively, triolein, a naturally-occurring triglyceride of high purity (available from Sigma Chemical Company, St. Louis, Mo.), or oils of animal or vegetable origin, such as soybean oil, safflower oil, cottonseed oil, fish oils, and the like.

In other preferred embodiments, the lipophilic core includes lipophilic or amphipathic bioactive agents which may be used for diagnostic or therapeutic purposes. For diagnostic purposes, exemplary agents include, but are not limited to, halogenated triglycerides, such as iodinated or fluorinated triglycerides, which may contain a stable or radioactive isotope of the halogen.

In particularly preferred embodiments, the lipophilic core includes a mixture of at least one pharmacologically inert oil and a bioactive or inactive agent in a molar ratio in the range of 0.3 to 2, and more preferably 1:1. Preferably, the lipophilicity of each core component is comparable to ensure suitable blending of the lipid components.

In iodinated embodiments, iodine-containing lipids, of the type known in the art, can be used. Such lipids include iodinated fatty acids in the form of glycerol or alkyl esters. However, in particularly preferred embodiments, the iodine-containing lipids are synthetic aromatic compounds of known purity which are stabilized against in vivo degradation of the iodine linkage. Illustrative examples of radioactive or non-radioactive halogenated triglycerides useful in the practice of the invention include, without limitation, iodinated triglycerides of the type described in U.S. Pat. No. 4,873,075 issued on Oct. 10, 1989; U.S. Pat. No. 4,957,729 issued on Sep. 18, 1990; and U.S. Pat. No. 5,093,043 issued on Mar. 3, 1992. Exemplary iodinated triglycerides are 2-oleoylglycerol-1,3-bis[7-(3-amino-2,4,6-triiodophenyl) heptanoate] (DHOG) and 2-oleoylglycerol-1,3-bis[4-(3-amino-2,4,6-triiodophenyl)butanoate] (DBOG).

Clinically, $^{122}$I, $^{123}$I, $^{125}$I, and $^{131}$I are the iodine isotopes most often used with currently available scanning instrumentation. Of course, $^{133}$I-radiolabeled triglycerides may be used for therapeutic purposes, as is known in the art. However, any radioactive isotope of iodine is within the contemplation of the invention. A listing of all iodine isotopes is available at pages B-303-B-305 of the *Handbook of Chemistry and Physics,* 58th edition, CRC Press, 1977–1978. It should be noted that $^{127}$I is the naturally-occurring stable isotope and is not considered to be "radioactive".

In fluorinated embodiments, specific examples include stable or radioactive ($^{19}$F) fluorinated triglycerides which are analogous to the iodinated triglycerides discussed above, illustratively glyceryl-2-oleoyl-1,3-bis(trifluoromethyl) phenyl acetate. In alternative embodiments of the invention, fluorine-containing lipids may be esters or triglycerides of perfluoro-t-butyl-containing fatty acid compounds, such as described in U.S. Pat. Nos. 5,116,599 and 5,234,680, illustratively, 7,7,7-trifluoro-6,6-bis (trifluoromethyl)-heptanoic acid or 8,8,8-trifluoro-7,7-bis(trifluoromethyl)-octanoic acid. Of course, these examples are merely illustrative of the many specific examples of lipophilic or amphipathic fluorinated compounds suitable for use in the practice of the invention, and are not in any way intended to be exclusive or limiting.

In still further embodiments of the invention, the bioactive agent may comprise brominated compounds, such as brominated ethyl esters of fatty acids or monobrominated perfluorocarbons.

Potential therapeutic agents for inclusion in the lipophilic core of the synthetic oil-in-water emulsion of the present invention include lipophilic derivatives of oligonucleotides or nucleic acids, or lipophilic and/or amphipathic derivatives of anti-cancer agents, such as esters of methotrexate, mitomycin C, fluorodeoxyuridine or doxorubicin.

The monolayer surrounding the nonpolar lipophilic core comprises up to about 10% (w/v) of a polar lipid monolayer component, which may be an emulsifier. Phospholipids of natural, synthetic, or semi-synthetic origin are suitable for use in the practice of the invention. Traditional lipid emulsions for delivery of bioactive agents use natural phospholipids, such as soy lecithin and egg phosphatidylcholine (e.g., Intralipid). In preferred embodiments of the present invention, the emulsion components are synthetic, semi-synthetic, and/or naturally occurring components of known origin, purity and relative concentrations. The improper use of egg lecithins (mixtures of phospholipids) and/or crude oils (cottonseed, poppy seed, and the like) in prior art emulsions may result in variable and non-reproducible compositions.

In a specific advantageous embodiment, dioleoylphosphatidylcholine (DOPC) is used as an emulsifier, or monolayer surfactant. DOPC is a semi-synthetic, chemically defined phospholipid emulsifier of high purity (available from Avanti Polar Lipids, Alabaster, Ala.). Of course, other surface active agents which are suitable for parenteral use can be substituted for all or a portion of the polar lipid monolayer component. The naturally-occurring phospholipids are advantageous because these phospholipids have a reasonable potential for interaction with apolipoproteins and an appropriate transition temperature, i.e., they are in the liquid state at physiologic temperatures.

The osmolality of the emulsion is adjusted to 400–500 mOsm/kg with up to 5% w/v of an osmolality adjusting agent, such as USP glycerol or glucose. The oil-in-water emulsion of the present invention produces a delivery vehicle which is nearly isotonic relative to blood. This is in sharp contrast to most commonly used ionic contrast media which have osmolalities 3 to 5 times higher than that of the blood which can result in pain and tissue injury at the site of injection.

The remainder of the emulsion formulation comprises the bulk or aqueous phase. In the practice of a preferred embodiment of the present invention, the aqueous phase is sterile water of a grade suitable for parenteral administration. The inclusion of salt (NaCl) in the aqueous phase, such as by the use of 0.9% saline, results in emulsions which have a mean particle diameter as much as twice the size of salt-free emulsions. Furthermore, the presence of salt in the formulation has an adverse effect on the ability of the emulsion to survive autoclave sterilization without a significant change in mean particle size as well as on the temporal stability of an autoclaved emulsion.

In addition to NaCl, pH-adjusting agents frequently used in the formulation of parenteral emulsions, such as NaOH or the sodium salts of most aqueous buffers, introduce excessive sodium ions into the bulk phase. These agents have been found to have deleterious effects on particle size, stability, and the ability to survive autoclaving.

Other conventional additives, such as antioxidants, buffers, preservatives, viscosity adjusting agents, and the like, may be included in the composition. In particular, up to 5% w/v of an antioxidant, such as α-tocopherol, flavinoids, BHT, or BHA, is recommended. However, the additive should not adversely affect the physical characteristics of the emulsion, such as particle size or shelf and heat stability.

The techniques used to formulate the oil-in-water emulsions of the present invention are important in achieving small particle diameter, uniform size distribution, lack of liposome contamination, etc. all of which contribute to hepatocyte-selectivity and heat stability.

In accordance with a method of making aspect of the invention, the lipophilic components of the oil-in-water emulsion including nonpolar core lipids, polar lipid emulsifiers, and other lipophilic components, such as bioactive or bioinactive agents, are blended together to form a preblended lipid phase. The aqueous components are combined and added to the preblended lipid phase. The preblended lipid phase and aqueous components are homogenized to form a crude oil-in-water emulsion. The crude oil-in-water emulsion is subjected to ultra high energy emulsification to produce a fine oil-in-water emulsion having a mean particle diameter of the oil phase between 50 to 200 nm with greater than 98% of the particles being less that 300 nm. In preferred embodiments of the invention, the fine oil-in-water emulsion is sequentially filtered.

In a preferred method aspect of the invention, the lipid components are initially blended or homogenized using a high speed mixer, such as a Polytron homogenizer (Kinematica GmbH, Lucerne, Switzerland) or Ultra Turrax (IKA-Works, Cincinnati, Ohio), operating at 12,500 rpm at 55° C. for at least 5 minutes. Then, the aqueous components are added to the preblended lipid components and pre-emulsified by high speed mixing or homogenization at 25,000 rpm under the same, or similar, conditions to form a crude emulsion. Final processing is accomplished with ultra high energy mixing equipment, such as a MicroFluidizer high pressure homogenizer (Model 110S, Microfluidics Corp., Newton, Mass.; see, USPN 4,533,254), or equivalent equipment, such as the Emulsiflex (Avestin Inc., Ottawa, Ontario, Canada) or the Manton-Gaulin (APV Gaulin Rannie, St. Paul, Minn.), operating in the recycling mode at 30°–60° C. and 10,000 to 30,000 psi, and preferably at about 12,500–18,200 psi, for up to about 20 minutes. After processing, the emulsion is passed sequentially through sterile 0.45 $\mu$m and 0.22 $\mu$m sterile filters. The sequential filtration removes any large particles and partially sterilizes the product.

The temperature for high energy mixing is illustrative, and should be chosen relative to the bioactive agent. In other words, the temperature should be greater than or equal to the transition temperature or melting point of the bioactive agent. An upper bound, however, is determined by whether the temperature would cause degradation or decomposition of any components in the composition.

The use of an ultra high pressure homogenizer ensures small particle size with a narrow size range distribution so that the resulting emulsion will simulate chylomicron remnants. Conventional systems for forming emulsions, such as homogenizers, sonicators, mills, and shaking systems provide a shearing force on the liquid components whereas the ultra high energy mixing equipment puts the emulsion components under pressure and forces them through small openings to reduce particle size. Size distribution may be measured by a Nicomp 370 Dynamic Laser Light Scattering Autocorrelator (Nicomp Particle Sizing Systems, Santa Barbara, Calif.) or similar equipment. A lipid emulsion, which is suitable for the practice of the present invention, will have a mean particle diameter less than about 300 nm, and preferably in the range of 50 to 200 nm as measured by Nicomp number weighting analysis. The particles should have a narrow size distribution, with about 98% of the particles being in the 50 to 300 nm. No particles should be detected with a diameter of greater than 1 $\mu$m.

The size distribution should be stable for a minimum shelf-life period of ninety days. By "shelf-stable" is meant that the mean diameter of the emulsion particles should not change by greater than 15% at 90 days post-formulation, or more than 20% over the shelf-life. The emulsion can be stored for up to 2 years at room temperature. Under ideal conditions, the product is stored under nitrogen at 4° to 8° C. and is, preferably, protected from light.

In preferred embodiments, the emulsion is sterilizable by heat or cold filtration, for example. Standard or intermittent autoclaving techniques, such as 20 minutes exposure to pressurized steam at 121° C., should not adversely affect the size distribution of the emulsion. As used herein the term "heat stable" means that the emulsion has the ability to withstand standard heat sterilization (e.g., 20 minutes exposure to steam at 121° C.) without a significant change in mean particle size distribution. A significant feature of the composition/formulation process of the present invention is the ability of the emulsion to retain its ability to associate apo E following autoclaving. Therefore, the term "heat stable" as used herein to define the microemulsion of the present invention includes the ability to associate with apo E after heat sterilization (see, Table 3).

In a method of use aspect of the invention, an oil-in-water emulsion of the present invention containing a contrast enhancing agent is administered to a mammal and the mammal is subjected to x-ray computed tomographic imaging after the emulsion has reached the target site. In alternative methods of use, appropriate oil-in-water emulsions, containing bioactive agents suitable for other diagnostic modalities, such as proton magnetic resonance imaging (MRI), $^{19}$F-MRI, or scintigraphy may be administered for visualization and/or detection. In still another method of use embodiment, a therapeutic agent, such as a $^{131}$I-containing triglyceride, is delivered to a target site in an oil-in-water emulsion of the present invention.

BRIEF DESCRIPTION OF THE DRAWINGS

Comprehension of the invention is facilitated by reading the following detailed description, in conjunction with the annexed drawings, in which.

DETAILED DESCRIPTION

Figure 1:
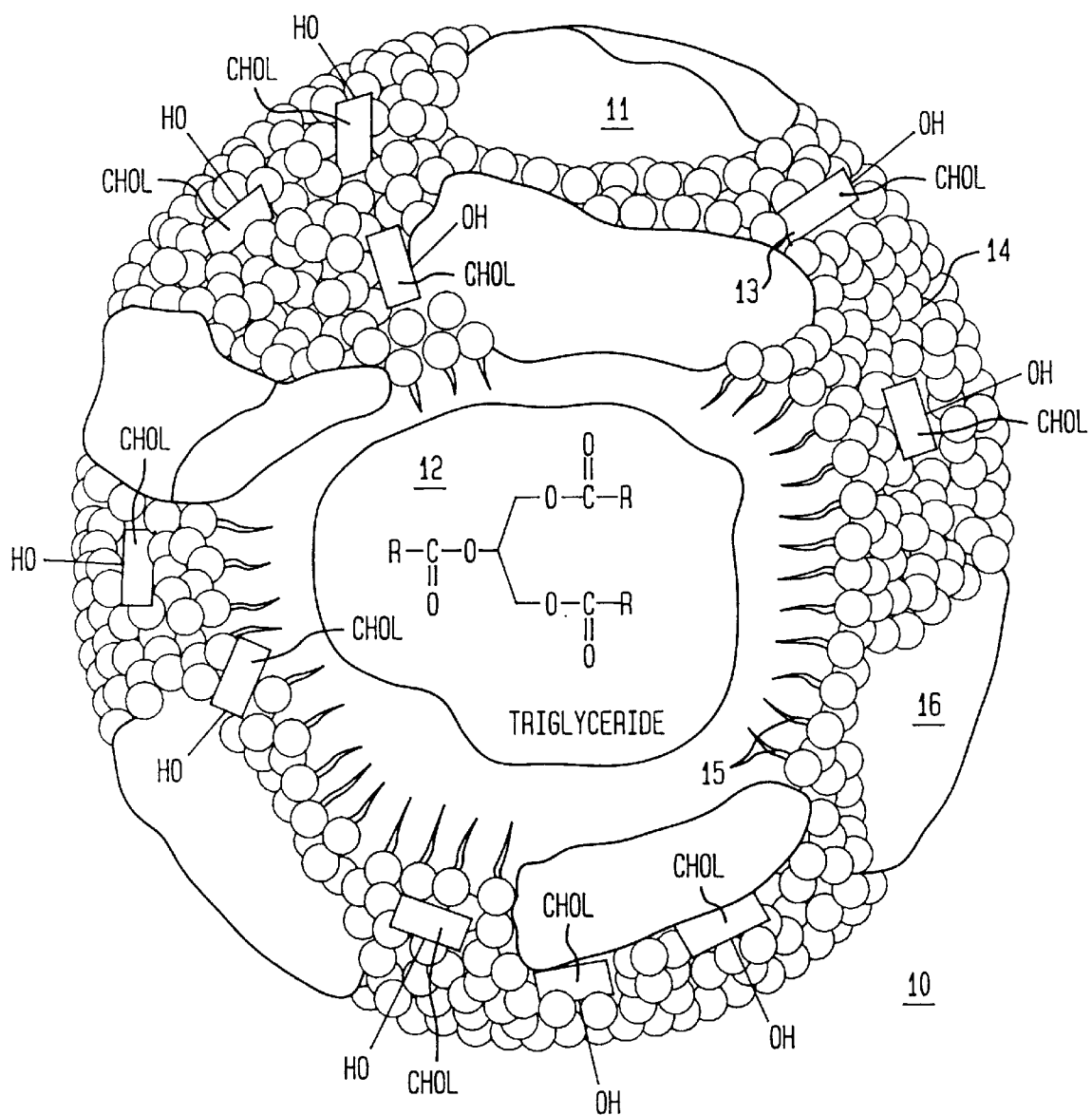
FIG. 1 is a diagrammatic representation of an oil phase particle of the oil-in-water emulsion of present invention.

FIG. 1 is a diagram of an oil phase particle 10 of the present invention. A lipophilic lipid core 12 is surrounded by a monolayer 11 consisting of an emulsifier and cholesterol 13. The lipid core contains a pharmacologically inert fat or oil, such as a triglyceride (e.g., triolein) and/or a lipophilic or amphipathic bioactive or bioinactive agent, such as a radiologic agent. The polar moieties (spheres 14, e.g., polar head portions of a phospholipid emulsifier) of the monolayer face outward into the bulk water phase (not specifically shown) whereas the nonpolar moieties (tails 15) of the monolayer are oriented toward the lipid core. A purely lipophilic compound to be delivered in accordance with the principles of the invention would reside entirely in the core of the lipid particle beneath the monolayer. On the other hand, an amphipathic compound, which has both lipophilic and hydrophilic components, would reside in the particle by interaction with both the core and the monolayer. For example, such an amphipathic agent might have a long lipophilic tail to tether a hydrophilic moiety to the particle. The lipophilic tail could intermix with the lipophilic tails of the phospholipid/cholesterol components of the monolayer or could extend into the core. FIG. 1 also shows large amorphous structures 16 which represent apolipoproteins.

The following specific examples illustrate some of the many possible oil-in-water emulsions which can be made in accordance with the principles of the invention.

Iodine Embodiments

Illustrative examples of radioactive or non-radioactive polyhalogenated triglycerides particularly suitable for use in the practice of the invention are described in U.S. Pat. No. 4,873,075 issued on Oct. 10, 1989; U.S. Pat. No. 4,957,729 issued on Sep. 18, 1990; and U.S. Pat. No. 5,093,043 issued on Mar. 3, 1992, the disclosures of which are incorporated by reference herein in their entirety. The iodinated arylaliphatic triglyceride analogs of the aforementioned patents have a triglyceride backbone structure which is 1,3-disubstituted or 1,2,3-trisubstituted with a 3-substituted 2,4,6-triiodophenyl aliphatic chain or a monoiodophenyl aliphatic chain. In preferred embodiments, all of the aliphatic chains, whether on the iodinated moiety or an open position on the triglyceride backbone structure, are saturated or unsaturated aliphatic hydrocarbon chains of the type found in naturally-occurring fatty acids. Naturally-occurring fatty acids may include those containing about 4–20 carbons, illustratively palmitic acid (16), palmitoleic acid (16:1), oleic acid (18:1), linoleic acid (18:2), arachidonic acid (20:4), etc.

Specific examples include, but are not limited to: glyceryl-2-palmitoyl-1,3-di-(3-amino-2,4,6-triiodophenyl) iopanoate; glyceryl-2-palmitoyl-1,3-di-(3-amino-2,4,6-triiodophenyl)dodecanoate; glyceryl-2-palmitoyl-1,3-di-(3-amino-2,4,6-triiodophenyl)acetate; glyceryl-2-palmitoyl-1,3-di-(3-amino-2,4,6-triiodophenyl)propionoate; glyceryl-1,2,3-triiopanoate; glyceryl-1,2,3-tri-12-(3-amino-2,4,6-triiodophenyl)dodecanoate; glyceryl-1,3-di-17-(3-amino-2,4,6-triiodophenyl)heptadecanoate; glyceryl-1,2,3-tri-3-(3-amino-2,4,6-triiodophenyl)propionate;glycerol-2-palmitoyl-1,3-di-15-(p-iodophenyl)pentadecanoate;glyceryl 2-oleoyl-1,3-di-(3-amino-2,4,6-triiodophenyl)-butyrate; glyceryl-2-oleoyl-1,3-di-(3-amino-2,4,6-triiodophenyl)-pentanoate, glyceryl 2-oleoyl-1,3-di-(3-amino-2,4,6-triiodophenyl)-hexanoate; glyceryl 2-oleoyl-1,3-di-(3-amino-2,4,6-triiodophenyl)-octanoate; glyceryl 2-oleoyl-1,3-di-(3-amino-2,4,6-triiodophenyl)-heptanoate, etc.

For the studies reported herein, iodinated triglycerides were synthesized and radioiodinated with $^{125}$I via isotope exchange in a melt of pivalic acid in accordance with a method known in the art. Of course, radioiodination of the iodinated triglycerides, or one of the intermediates in their synthesis pathway, can be accomplished by a variety of techniques, known to those of skill in the art.

EXAMPLE 1

Figure 2:
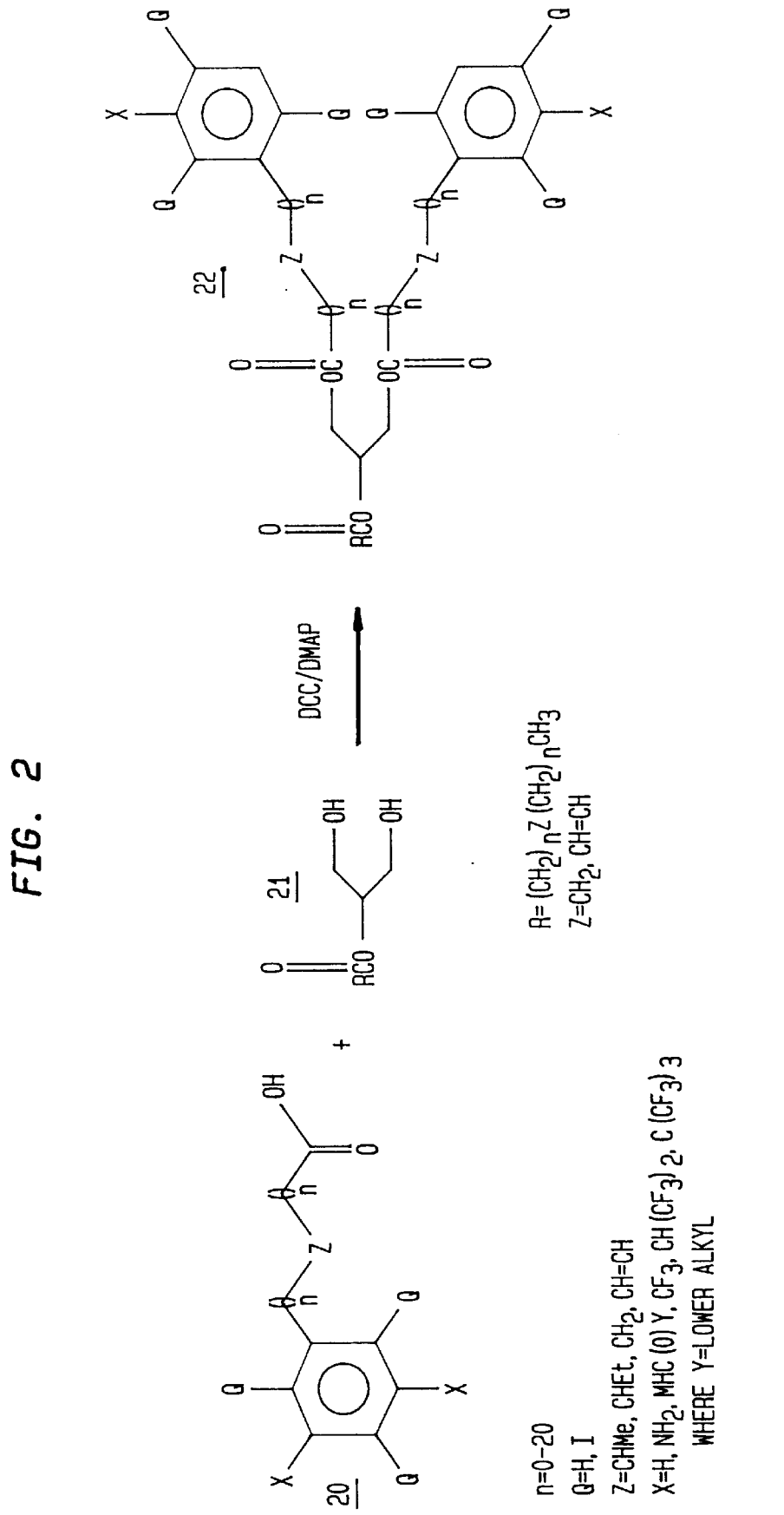
FIG. 2 is an illustrative preparatory scheme for a series of fluorinated or iodinated triglycerides, specifically 1,3-disubstituted triacylglycerols, suitable for use in the practice of the present invention.

A series of iodinated triglycerides of the following general formula, specifically 1,3-disubstituted triacylglycerols, which are identified as Compounds 1–7 in Table 1, were synthesized in accordance with the illustrative preparatory scheme shown on FIG. 2.

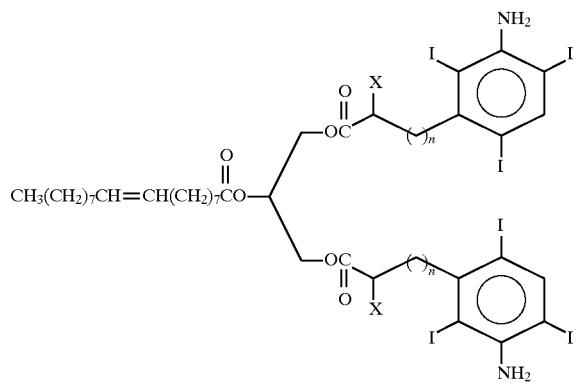

TABLE 1

| Compound | n | X | Chemical Name |
|---|---|---|---|
| 1 | 0 | H | 2-oleoylglycerol-1,3-[bis-(3-amino-2,4,6-triiodophenyl)acetate] |
| 2 | 1 | H | 2-oleoylglycerol-1,3-[bis-(3-amino-2,4,6-triiodophenyl-propionate] |
| 3 | 1 | ethyl | 2-oleoylglycerol-1,3-bis[iopanoate] |
| 4 | 2 | H | 2-oleoylglycerol-1,3-bis[4-(3-amino-2,4,6-triiodophenyl)butyrate] |
| 5 | 3 | H | 2-oleoylglycerol-1,3-bis[5-(3-amino-2,4,6-triiodophenyl)pentanoate] |
| 6 | 4 | H | 2-oleoylglycerol-1,3-bis[6-(3-amino-2,4,6-triiodophenyl)hexanoate] |
| 7 | 5 | H | 2-oleoylglycerol-1,3-bis[7-(3-amino-2,4,6-triiodophenyl)heptanoate] |

Referring to FIG. 2, a general reaction scheme is shown for a series of iodinated or fluorinated triglycerides, specifically 1,3-disubstituted triacylglycerols suitable for use in the practice of the present invention (Compounds 22). In the illustrative embodiments of Example 1, Compounds 22 are 2-oleoylglycerol-1,3-bis-[3-amino-2,4,6-triiodophenyl) alkanoates], designated as Compounds 1–7 on Table 1, which were synthesized via dicyclohexylcarbodiimide/4-dimethylaminopyridine (DCC/DMAP) coupling of a 2-monoolein (Compounds 21) with 2 equivalents of the corresponding ω-(3-amino-2,4,6-triiodophenyl)alkanoic acid (Compounds 20) as described below. ps Preparation of ω-(3-amino-2,4,6-triiodophenyl)alkanoic acids:

Synthesis of the ω-(3-amino-2,4,6-triiodophenyl)alkanoic acids (Compounds 20) was accomplished in a similar fashion to existing literature procedures (see, for example, Weichert, et al., *J. Med. Chem.*, Vol. 29, p. 1674 and 2457 (1986). Iopanoic acid is commercially available and was purchased from CTC Organics, Atlanta, Ga.

Preparation of 2-oleoylglycerol-1,3-bis-[3-amino-2,4,6-triiodophenyl)alkanoates]:

A rapidly stirred suspension of 2-monoolein (1,2,3-trihydroxypropane 2-oleate; 1.0 equiv), the ω-(3-amino-2,4,6-triiodophenyl)alkanoic acids (2.05–2.1 equiv), and a catalytic amount of DMAP (0.1 equiv) in anhydrous $CH_2Cl_2$ (5 ml/mmol of alcohol) was treated with DCC (1.1 equiv to acid). The resulting mixture was stirred under $N_2$ overnight at room temperature, diluted with $CH_2Cl_2$ and filtered to remove precipitated dicyclohexyl urea. The filtrate was washed with 0.5N HCl, saturated aqueous $NaHCO_3$, $H_2O$, and brine, and then dried ($MgSO_4$). The solvent was removed in vacuo, and the remaining residue was purified by column chromatography to afford the desired triacylglycerols.

Compound 1: 2-oleoylglycerol-1,3-bis[2-(3-amino-2,4,6-triiodophenyl)acetate]

Treatment of a mixture of 2-(3-amino-2,4,6-triiodophenyl)acetic acid (1.50 g, 2.8 mmol), 2-monoolein (481 mg, 1.35 mmol), and DMAP (37 mg) in anhydrous $CH_2Cl_2$, (20 ml) with DCC (635 mg, 3.1 mmol) according to the procedure described above gave a solid residue (1.56 g), which was purified by column chromatography on silica gel (4.5×30 cm) eluted with hexanes/EtOAc/$CHCl_3$ (35:10:5) to give Compound 1 as a slightly yellow oil which resisted crystallization: yield 600 mg (32%); IR ($CHCl_3$) 3435, 3325 (amine), 2900, 2830 (aliphatic CH), 1730 (ester C=O) $cm^{-1}$; $^1$H NMR (270 MHz, $CDCl_3$) 8.05 (s,2 H, aryl 5-H's), 5.4–5.2 (m,3 H, CH=CH, glycerol 2-H), 4.80 (s, 4 H, $NH_2$), 4.32 (dd, 2 H, glycerol $OCH_AH_BCH(O)CH_AH_BO$), 4.24 (s, 4 H, $PhCH_2$'s), 4.15 (dd, 2 H, glycerol $OCH_AH_BCH(O)CH_AH_BO$), 2.30 (m, 6 H, $CH_2CO_2$ and =$CHCH_2$'s), 2.0–1.0 (m, 22 H, $CH_2$ envelope), 0.88 (t, 3 H, $CH_3$).

Anal ($C_{37}H_{48}O_6N_2I_6$) C, H.

Compound 2: 2-oleoylglycerol-1,3-bis[3-(3-amino-2,4,6-triiodophenyl)propionate]

Treatment of a mixture of 3-(3-amino-2,4,6-triiodophenyl)propionic acid(1.16 g, 2.1 mmol), 2-monoolein (356 mg, 1.0 mmol), and DMAP (24 mg) in anhydrous $CH_2Cl_2$(15 ml) with DCC (444 mg, 2.15 mmol) according to the procedure described above gave a residue (1.50 g), which was purified by column chromatography on silica gel (4.5×30 cm) eluted with hexanes/EtOAc/$CHCl_3$ (16:2:1) to give Compound 2 as a slightly yellow oil which resisted crystallization: yield 1.30 g (92%); IR ($CHCl_3$) 3440, 3330 (amine), 2905, 2830 (aliphatic CH), 1732 (ester C=O) $cm^{-1}$; $^1$H NMR (270 MHz, $CDCl_3$) 8.05 (s,2 H, aryl 5-H's), 5.4–5.2 (m,3 H, CH=CH, glycerol 2-H), 4.83 (s, 4 H, $NH_2$'s), 4.34 (dd, 2 H, glycerol $OCH_AH_BCH(O)CH_AH_BO$), 4.15 (dd, 2 H, glycerol $OCH_AH_BCH(O)CH_AH_BO$), 3.38 (dt, 4 H, $PhCH_2$'s), 2.55 (dt, 4 H, OC(O)$CH_2$'s), 2.35 (t, 6 H, oleoyl $CH_2CO_2$ and =$CHCH_2$'s), 1.99 (pst, 4 H, $CH_2$'s), 1.29 (m, 22 H, $CH_2$ envelope), 0.88 (t, 3 H, $CH_3$).

Anal ($C_{39}H_{52}O_6N_2I_6$) C, H.

Compound 3: 2-oleoylglycerol-1,3-bis[iopanoate]

Stirring a mixture of iopanoic acid (8.41 g, 14.7 mmol), 2-monoolein (2.50 g, 7.0 mmol), and DMAP (170 mg) in anhydrous $CH_2Cl_2$ (70 ml) with DCC (3.33 g, 16.0 mmol) according to the procedure described above for three days gave a residue (12.6 g), which was purified by column chromatography on silica gel (10×23 cm) eluted with hexanes/EtOAc/$CHCl_3$ (35:10:5) to give Compound 3 as a nearly colorless oil which resisted crystallization: yield 5.37 g (53%); IR ($CHCl_3$) 3470, 3370 (amine), 2930, 2860 (aliphatic CH), 1740 (ester C=O) $cm^{-1}$; $^1$H NMR (270 MHz $CDCl_3$) 8.07 (d, 2 H, aryl 5-H's), 5.32 (m, 2 H, CH=CH), 5.19 (m, 1 H, glycerol CH), 4.85 (s, 4 H, $NH_2$), 4.30 (m, 2 H, glycerol $OCH_AH_BCH(O)CH_AH_BO$), 4.10 (m, 2 H, glycerol $OCH_AH_BCH(O)CH_AH_BO$), 3.32 (dq, 4 H, $PhCH_2$'s), 2.78 (m, 2 H, iopanoyl $CHCO_2$), 2.28 (t, 2 H, oleoyl $CH_2CO_2$), 2.05 (m, 4 H, allylic $CH_2$'s), 1.85 (m, 2 H, iopanoyl $CHCH_AH_BCH_3$),1.56 (m, 2 H, iopanoyl $CHCH_AH_BCH_3$), 1.4–1.2 (m, 20 H, $CH_2$ envelope), 0.88 (t, 9 H, $CH_3$).

Anal ($C_{43}H_{60}O_6N_2I_6$) C, H.

Compound 4: 2-oleoylglycerol-1,3-bis[4-(3-amino-2,4,6-triiodophenyl)butanoate]

Stirring a mixture of 4-(3-amino-2,4,6-triiodophenyl) butanoic acid(7.00 g, 12.6 mmol), 2-monoolein (2.19 g, 6.1 mmol), and DMAP (168 mg) in anhydrous $CH_2Cl_2$ (80 ml) with DCC (2.85 g, 13.8 mmol) according to the procedure described above for three days gave a residue (12.5 g), which was purified by column chromatography on silica gel (1×25 cm) eluted initially with 1 liter of hexanes/EtOAc (5:1) and then with hexanes/EtOAc/$CHC_3$ (75:15:10) to give Compound 4 as a slightly yellow oil which resisted crystallization: yield 5.08 g (58%); IR ($CHC_3$) 3470, 3370 (amine), 2930, 2860 (aliphatic CH), 1740 (ester C=O) $cm^{-1}$; $^1$H NMR (270 MHz $CDCl_3$) 8.04 (s, 2 H, aryl 5-H's), 5.33 (m, 3 H, CH=CH, and glycerol 2-H), 4.81 (s, 4 H, NH2), 4.33 (m, 2 H, glycerol $OCH_AH_BCH(O)CH_AH_BO$), 4.20 (m, 2 H, glycerol $OCH_AH_BCH(O)CH_AH_BO$), 3.06 (m, 4 H, $PhCH_2$'s), 2.48, (t, 4 H, )$O_2CCH_2$'s), 2.33 (t, 2 H oleate $O_2CCH_2$), 2.00 (m, 4 H, allylic $CH_2$'s), 1.84 (m, 4 H, $PhCH_2CH_2$), 1.26 (d, $CH_2$ envelope), 0.89 (t, 3 H, $CH_3$).

Anal ($C_{41}H_{56}O_6N_2I_6$) C, H.

Compound 5: 2-oleoylglycerol-1,3-bis[5-(3-amino-2,4,6-triiodophenyl)pentanoate]

DCC (635 mg, 3.1 mmol) was added to a stirred suspension of 5-(3-amino-2,4,6-triiodophenyl)pentanoic acid(1.60 g, 2.8 mmol), 2-monoolein (480 mg, 1.3 mmol), and DMAP (50 mg) in anhydrous $CH_2Cl_2$ (45 ml) according to the procedure described above for 36 hours. Following workup, a residue (12.5 g) was obtained, which was purified by column chromatography on silica gel (4.6×42 cm) eluted with hexanes/EtOAc/$CHCl_3$ (80:15:5) to give Compound 5 as a slightly yellow oil which resisted crystallization: yield 1.35 g (71%); IR ($CHCl_3$) 3475, 3375 (amine), 2940, 2850 (aliphatic CH), 1738 (ester C=O) $cm^{-1}$; $^1$H NMR (360 MHz, $CDCl_3$) 8.03 (s, 2 H, aryl 5-H's), 5.26 (m, 3 H, CH=CH, and glycerol 2-H), 4.79 (s, 4 H, $NH_2$), 4.31 (m, 2 H, glycerol $OCH_AH_BCH(O)CH_AH_BO$), 4.16 (m, 2 H, glycerol $OCH_AH_BCH(O)CH_AH_BO$), 3.02 (m, 4 H, $PhCH_2$'s), 2.43 (t, 4 H, $O_2CCH_2$'s), 2.30 (t, 2 H, oleate $O_2CCH_2$), 2.01 (m,4 H, allylic $CH_2$'s), 1.80 (m, 4 H, $PhCH_2CH_2$'s), 1.62–1.24 (m, $CH_2$ envelope), 0.86 (t, 3 H, $CH_3$).

Anal ($C_{43}H_{60}O_6N_2I_6$) C, H.

Compound 6: 2-oleoylglycerol-1,3-bis[6-(3-amino-2,4,6-triiodophenyl)hexanoate]

DCC (801 mg, 3.9 mmol) was added to a stirred suspension of 6-(3-amino-2,4,6-triiodophenyl)hexanoic acid(2.14 g, 3.7 mmol), 2-monoolein (620 mg, 1.7 mmol), and DMAP (70 mg) in anhydrous $CH_2Cl_2$(45 ml) according to the procedure described above for 48 hours. Following workup, a residue (3.26 g) was obtained, which was purified by column chromatography on silica gel (3×25 cm) eluted with hexanes/EtOAc/$CHCl_3$(80:15:5) to give Compound 6 as a slightly yellow oil which resisted crystallization: yield 2.04 g (81%); IR ($CHCl_3$) 3475, 3375 (amine), 2940, 2850 (aliphatic CH), 1738 (ester C=O) $cm^{-1}$; $^1$H NMR (360 MHz, $CDCl_3$) 8.03 (s, 2 H, aryl 5-H's), 5.30 (m, 3 H, CH=CH, and glycerol 2-H), 4.79 (s, 4 H, $NH_2$), 4.31 (m, 2 H, glycerol $OCH_AH_BCH(O)CH_AH_BO$), 4.16 (m, 2 H, glycerol $OCH_AH_BCH(O)CH_AH_BO$), 3.01 (m, 4 H, $PhCH_2$'s), 2.34 (m, 6 H, $O_2CCH_2$'s and oleate $O_2CCH_2$), 2.00 (m,4 H, allylic $CH_2$'s), 1.72 (m, 4 H, $PhCH_2CH_2$'s), 1.60, 1.50, 1.27 (m, $CH_2$ envelope), 0.87 (t, 3 H, $CH_3$).

Anal ($C_{45}H_{64}O_6N_2I_6$) C, H.

Compound 7: 2-oleoylglycerol-1,3-bis[7-(3-amino-2,4,6-triiodophenyl)heptanoate]

DCC (3.62 g, 17.5 mmol) was added to a stirred suspension of 7-(3-amino-2,4,6-triiodophenyl)heptanoic acid(10.0 g, 16.7 mmol), 2-monoolein (2.83 g, 7.9 mmol), and DMAP (180 mg) in anhydrous $CH_2Cl_2$(120 ml) according to the procedure described above for 24 hours. Following workup, a residue (14.7 g) was obtained, which was purified by column chromatography on silica gel (10×25 cm) eluted with hexanes/EtOAc/$CHCl_3$ (80:15:5) to give Compound 7 as a slightly yellow oil which resisted crystallization: yield 9.45 g (79%); IR (CHCl$_3$) 3450, 3359 (amine), 2915, 2840 (aliphatic CH), 1740 (ester C=O) cm$^{-1}$; $^1$H NMR (360 MHz, CDCl$_3$) 8.03 (s, 2 H, aryl 5-H's), 5.30 (m, 3 H, CH=CH, and glycerol 2-H), 4.79 (s, 4 H, NH$_2$), 4.31 (m, 2 H, glycerol OCH$_A$H$_B$CH(O)CH$_A$H$_B$O), 4.16 (m, 2 H, glycerol OCH$_A$H$_B$CH(O)CH$_A$H$_B$O), 3.00 (m, 4 H, PhCH$_2$'s), 2.32 (m, 6 H, O$_2$CCH$_2$'s and oleate O$_2$CCH$_2$), 2.00 (m, 4 H, allylic CH$_2$'s), 1.72 (m, 4 H, PhCH$_2$CH$_2$'s), 1.61–1.26 (m, CH$_2$ envelope), 0.88 (t, 3 H, CH$_3$).

Anal (C$_{47}$H$_{68}$O$_6$N$_2$I$_6$) C, H.

The iodinated triglycerides of Example 1 were incorporated into the lipid core of an oil-in-water emulsion by formulation techniques in accordance with the invention as set forth more completely in the following examples.

EXAMPLE 2

In a specific illustrative embodiment, Compound 7 in Example 1, which is DHOG, was formulated into an oil-in-water emulsion for use as a hepatocyte-selective CT agent. The general formula is as follows:

10% (w/v) Total Lipid triolein (TO)+DHOG TO:DHOG (w/w)=1:1

2.4% (w/v) phospholipid DOPC 0.5% (w/v)% cholesterol Cholesterol:DOPC (molar ratio) =0.4

5% (w/v) USP glycerol 0.6% (w/v) α-tocopherol sterile water as bulk aqueous phase In terms of actual quantities, these concentrations and ratios translate to:

500.00 mg triolein 500.00 mg DHOG 2.40 ml of 100 mg/ml DOPC in absolute ethanol 47.10 mg cholesterol 500.00 mg USP glycerol 61.90 mg α-tocopherol (added just after the cholesterol)

total to 10 ml sterile water

The solid lipids and purified oils were weighed into a 50 ml glass tube followed by the addition of 2.40 ml of 100 mg/ml DOPC in ethanol and 5 mls of ethyl acetate. The solvent was removed by evaporation under vacuum at 40° C. for about 10 minutes on a rotary evaporator. The tube was removed from the rotary evaporator and 500.0 mg triolein were added on top of the DOPC. 47.10 mg cholesterol were then added to the DOPC/TO mixture. Next, 500.0 mg DHOG were added to the lipid mixture. Finally, about 3 ml CHCl$_3$ were added to the tube to facilitate complete mixing of the lipids. Organic solvents, such as ethanol, ethyl acetate, or chloroform, are used only as necessary to introduce lipophilic, lipophobic, or amphipathic components into the emulsion.

The lipids were rinsed from the walls of the tube with 1 ml of ethyl acetate:ethanol (2:1) and the tube was returned to the rotary evaporator to remove the solvent under vacuum at 40° C. for about 30 minutes. The rotary evaporator was connected to a high vacuum line for another 40–45 minutes.

A 500 mg aliquot of glycerol was added to the lipid mixture. The components were processed on the Polytron under a stream of nitrogen. Initial emulsification of this mixture was done at 12,500 rpm for 5 minutes at less than 55° C. followed by the addition of the aqueous phase (about 6 ml sterile water). After the water was added, the emulsion was processed for 5 minutes at full speed (25,000 rpm) using the Polytron. The emulsion was rinsed from the generator with a small volume of sterile water and the contents were transferred to a gas-tight syringe. A final volume of 10.0 ml emulsion was obtained by the addition of sterile water.

The emulsion was transferred to the MicroFluidizer 110S sample reservoir and the emulsion was processed at 34–36° C. for 10 minutes at 14,700 psi using the continuous pass mode. Processed emulsion was collected from the unit, filtered through a 0.45 μm Acrodisc filter and then filtered through a 0.22 μm Acrodisc sterile filter directly into a sterile multidose vial. The vial was stored overnight at room temperature prior to particle sizing.

Figure 3:
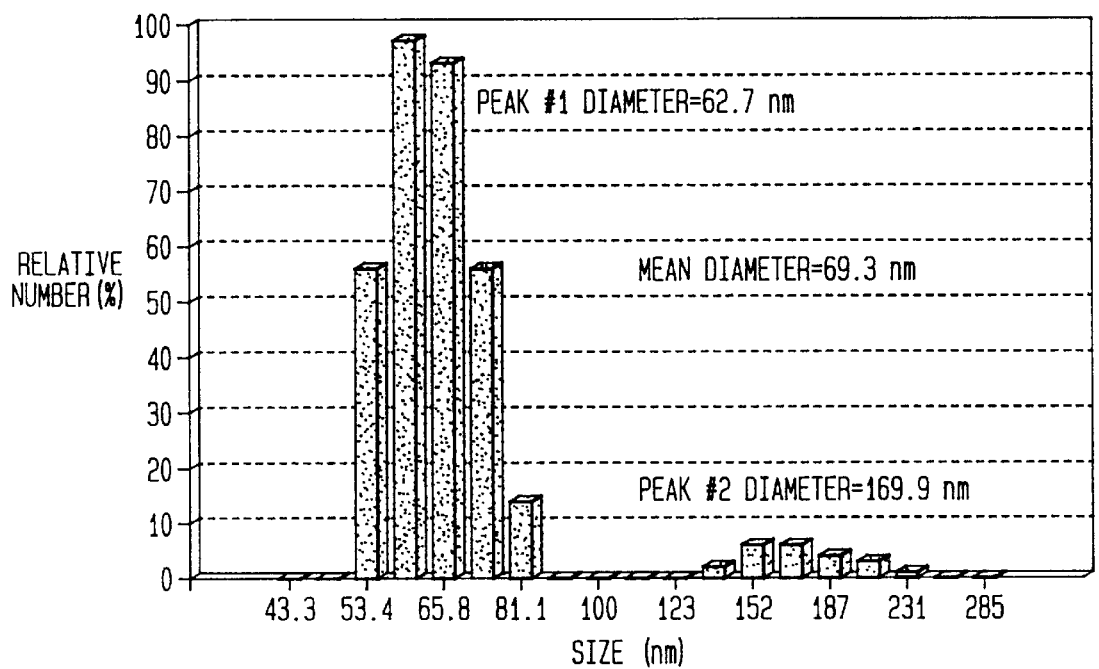
FIG. 3 is a graphic representation of a typical distribution of the oil phase particle size, in nm, in an emulsion of the present invention as measured by Nicomp Number Weighting analysis.
Figure 4:
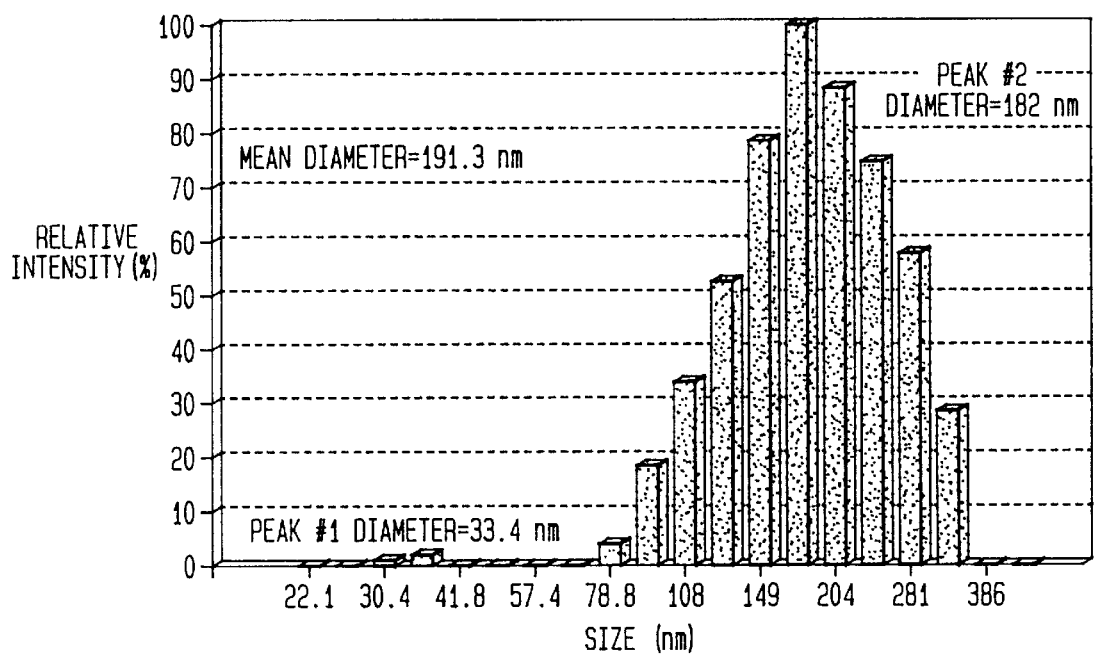
FIG. 4 is a graphic representation of a typical distribution of the oil phase particle size, in nm, in an emulsion of the present invention as measured by Nicomp Intensity Weighting analysis.

In accordance with the present invention, the mean diameter of oil phase particles is between 50 and 200 nm (number weighted), with a narrow distribution wherein no more than 2% of the particles have a diameter that falls outside of the range (i.e., being greater than 300 nm). Typical distributions of the particle size in an emulsion of the present invention are shown graphically in FIG. 3 (Nicomp Number Weighting analysis) and FIG. 4 (Nicomp Intensity Weighting analysis). The data are presented in both Nicomp Intensity and Nicomp Number weighted formats to enable determination of not only the diameter at which most of the particles exist (number weighting), but also the presence of small, but significant populations of large particles (intensity weighting). The distribution should not have any particles greater than 1 μm. Nor should the emulsion contain more than a minimal amount of liposomes.

The molar ratio of cholesterol to emulsifier, which in this case is DOPC, directly affects the particle diameter. The preferred molar ratio of cholesterol to phospholipid for achieving an emulsion which successfully mimics chylomicron remnants is in the range of 0.05 to 0.70, and more specifically at 0.40 for hepatocyte-selective delivery of iodinated triglycerides as demonstrated in FIGS. 5 and 6.

Figure 5:
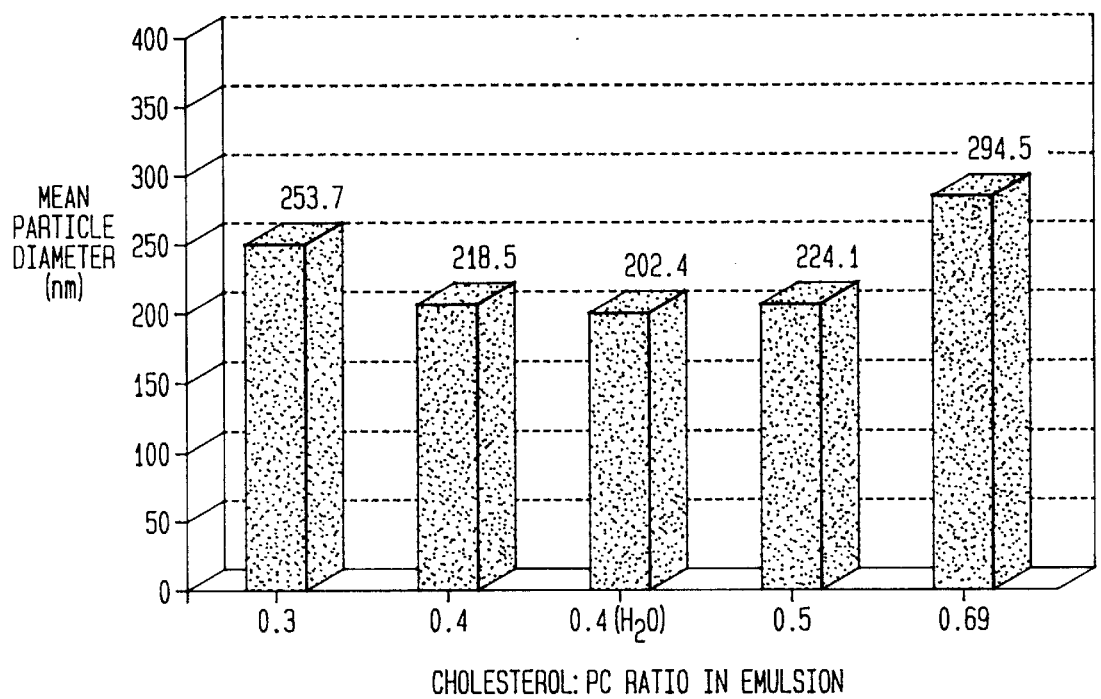
FIG. 5 is a graphic representation of the mean particle diameter (nm) for microemulsions containing 10% core lipids (w/v), including 5% triolein and 5% iodinated triglyceride (DHOG), 2.4% (w/v) phospholipid (DPOC) and varying amounts of cholesterol, so that the molar ratio of cholesterol to phospholipid ranges from 0.3 to 0.69.

FIG. 5 is a graphic representation of the mean particle diameter (nm) of a 10% triglyceride emulsion containing 5% triolein (w/v) and 5% (w/v) iodinated triglyceride (DHOG), 2.4% (w/v) phospholipid (DPOC) and varying amounts of cholesterol, so that the molar ratio of cholesterol to phospholipid ranges from 0.3 to 0.69. The microemulsions containing a molar ratio of 0.4 exhibited the smallest mean particle diameter (202.4 nm), but the remaining microemulsions had particles sizes which were acceptable.

Figure 6:
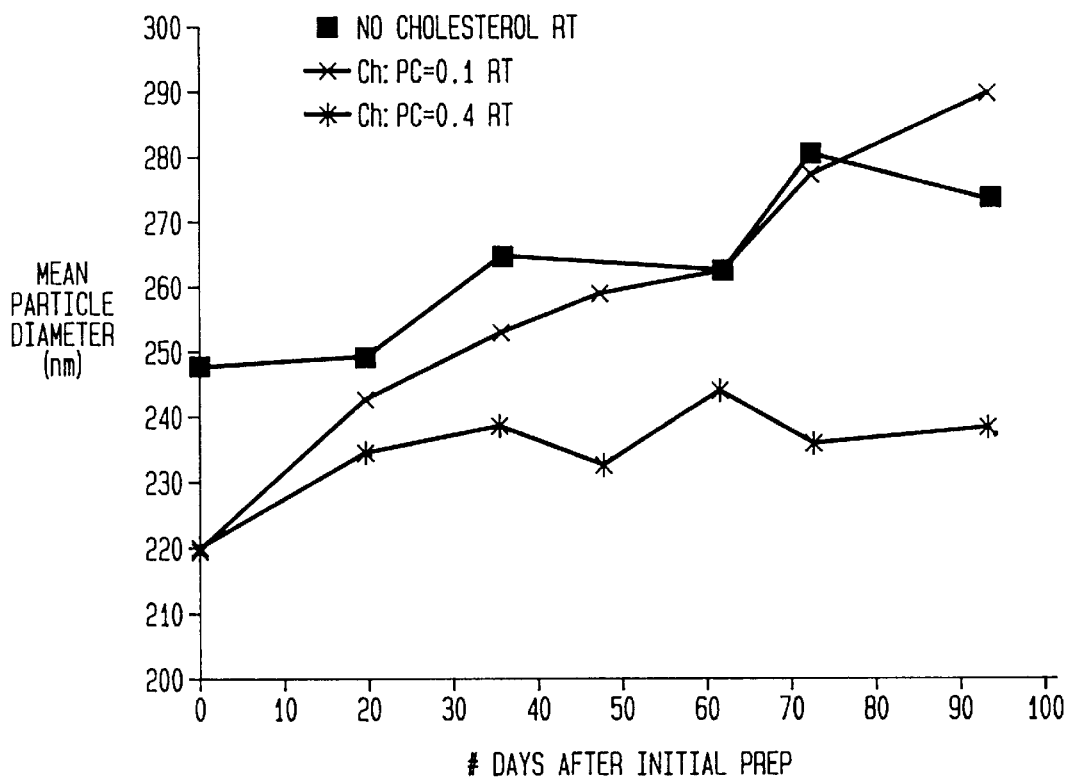
FIG. 6 is a graphic representation of the mean particle diameter (nm) as a function of time (days) post-formulation of microemulsions of the type shown in FIG. 5 and containing no cholesterol or cholesterol in a molar ratio of cholesterol to phospholipid of 0.1 or 0.4.

FIG. 6 is a graphic representation of the mean particle diameter (nm) as a function of time (days) post-formulation for 10% emulsions containing 5% triolein and 5% iodinated triglyceride (DHOG), 2.4% phospholipid (w/v) and varying amounts of cholesterol. Referring to FIG. 6, the microemulsion containing a molar ratio of cholesterol to phospholipid of 0.4 ("*") showed shelf stability over a 90 day test period whereas the microemulsions containing no cholesterol ("■") or a molar ratio of cholesterol to phospholipid of 0.1 ("◊") were not shelf stable. Thus, the appropriate amount of cholesterol contributes to shelf stability.

Figure 7:
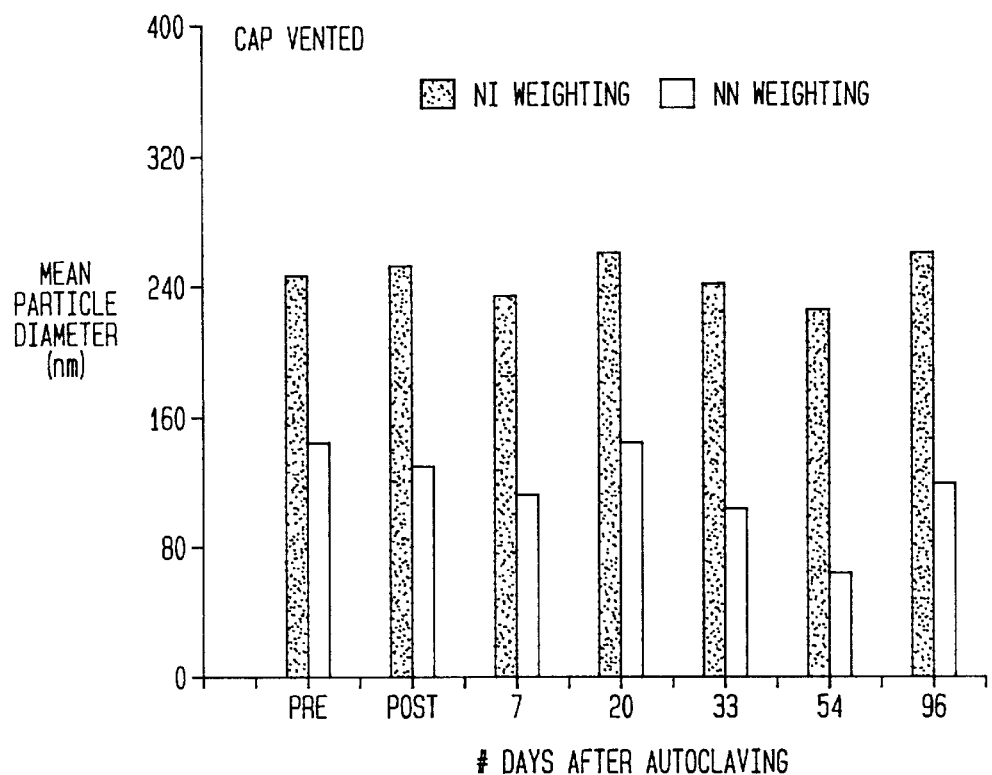
FIG. 7 is a graphic representation of the mean particle diameter (nm) of the microemulsion shown in FIG. 6 (CH:PC=0.4) as a function of time before and after steam sterilization in an autoclave.

Cholesterol also stabilizes the monolayer to resist changes in diameter following heat sterilization. FIG. 7 is a graphic representation of the mean particle diameter (nm) of the emulsion of Example 2 as a function of time before and after steam sterilization in an autoclave.

The data are expressed in both intensity and number weighted formats. Emulsions prepared without cholesterol did not survive autoclave sterilization.

EXAMPLE 3

Biodistribution Studies

Radioactive emulsions of the iodinated triglyceride compounds of Example 1 (see Table 1) were prepared by the technique set forth in Example 2. The microemulsions were administered intravenously (tail vein) to normal female Sprague-Dawley rats at a radiologic dose of 25–45 mg I/kg body weight for biodistribution studies. Following injection, groups of animals were sacrificed at various time points (30 minutes, 3 hours, and 24 hours) and the appropriate tissues were removed, rinsed free of blood, and analyzed for radioactivity. The liver, spleen, and blood values are listed in Table 2 as the percent administered dose per organ±SEM (based on the actual organ weights for each animal, n=3, and the literature values for the blood as a percent of total body weight). Other tissues, including kidney, lung, bone marrow, ovaries, adrenals, thyroid, heart, fat, and muscle generally contained low levels of radioactivity.

Liver density decreased slightly for Compound 3 by 24 hours, but had returned nearly to baseline for Compound 7.

The presence of hypodense liver tumors ranging in size from 1 to 15 mm in diameter were readily detected in CT studies of tumor-bearing rats (Morris Hepatoma 7777). Peak liver densities persisted for up to 2 hours with Compound 7 and for over 24 hours with Compound 3. In both cases, the imaging characteristics were similar to or exceeded those observed following administration of a urographic control (Omnipaque 300, Sanofi/Winthrop, New York, N.Y.; at a dose of 600 mgI/Kg body weight). However, the contrast agents of the present invention produced images with less than one-tenth the iodine dose.

Figure 8:
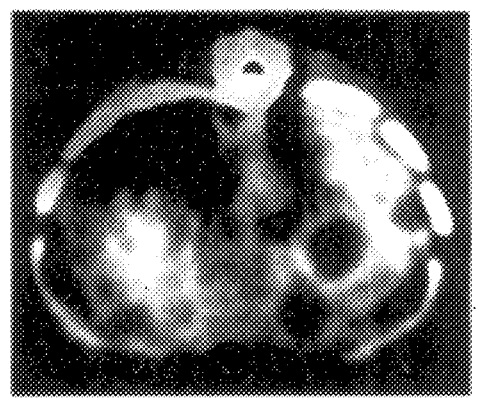
FIG. 8 is an axial CT image (3 mm slice thickness) of tumor-bearing rat (Morris Hepatoma 7777) taken at 60 minutes after administration of a CT contrast producing agent which is an oil-in-water emulsion in accordance with the present invention.

FIG. 8 is an axial CT image (3 mm slice thickness) of one tumor-bearing rat 60 minutes after administration of the

TABLE 2

| Cmpd.  | 1            | 2            | 3            | 4            | 5            | 6            | 7           |
|--------|--------------|--------------|--------------|--------------|--------------|--------------|-------------|
|        |              |              |              | 30 min       |              |              |             |
| liver  | 69.8 ± 7.1   | 66.2 ± 4.9   | 78.0 ± 2.5   | 75.4 ± 3.6   | 65.1 ± 2.2   | 66.8 ± 2.4   | 67.7 ± 6    |
| spleen | 12.0 ± 1.1   | 13.0 ± 0.2   | 14.4 ± 0.8   | 13.7 ± 1.1   | 9.5 ± 0.8    | 13.9 ± 0.5   | 10.5 ± 2    |
| blood  | 7.6 ± 2.3    | 5.1 ± 2.0    | 2.6 ± 0.8    | 5.8 ± 3.5    | 0.9 ± 0.3    | 4.8 ± 1.2    | 6.6 ± 3     |
|        |              |              |              | 3 hour       |              |              |             |
| liver  | 79.0 ± 0.3   | 71.7 ± 0.6   | 80.0 ± 8.0   | 93.4 ± 4.3   | 60.7 ± 2.9   | 66.0 ± 1.9   | 45.8 ± 2    |
| spleen | 14.5 ± 1.2   | 12.9 ± 0.8   | 11.3 ± 1.4   | 11.7 ± 2.9   | 8.0 ± 0.4    | 11.3 ± 0.4   | 8.2 ± 1     |
| blood  | 0.5 ± 0.1    | 0.7 ± 0.0    | 0.3 ± 0.0    | 0.9 ± 0.0    | 0.9 ± 0.7    | 2.2 ± 0.3    | 2.7 ± 0     |
|        |              |              |              | 24 hour      |              |              |             |
| liver  | 72.5 ± 0.3   | 69.8 ± 1.7   | 77.0 ± 3.4   | 74.3 ± 1.6   | 36.1 ± 1.6   | 34.9 ± 3.4   | 9.6 ± 1     |
| spleen | 12.2 ± 1.2   | 11.2 ± 2.2   | 12.5 ± 1.0   | 8.8 ± 0.5    | 6.4 ± 0.3    | 5.8 ± 0.7    | 0.8 ± 0     |
| blood  | 0.2 ± 0.0    | 0.5 ± 0.2    | 0.9 ± 0.1    | 1.5 ± 0.0    | 1.4 ± 0.1    | 1.1 ± 0.2    | 2.5 ± 0     |

All seven analogs displayed a high degree of liver specificity as demonstrated in the tissue distribution results reported in Table 2. From 65 to 78 percent of the radioactivity of the injected dose resided in the liver 30 minutes after administration. At 3 hours, from 46 to 93 percent of the radioactivity remained in the liver. Liver to blood ratios at 3 hours ranged from 11 to 400 based on calculations of injected dose per gram of tissue. The longer chain analogs (Compounds 5–7) appeared to have undergone some degree of metabolism and subsequent elimination from the liver by 3 hours. The shorter chain analogs (Compounds 1–4), on the other hand, appeared to be more resistant to in vivo metabolism and elimination from the liver as indicated by a relatively small decrease in liver radioactivity at 3 hours as compared to 24 hours. Thus, while liver uptake is primarily dependent on the characteristics of the emulsion vehicle, metabolism and subsequent clearance of the targeted triglyceride analog from the liver may be influenced, at least in part, by the chemical structure of the triglyceride, including the alkyl chain length. Shorter chain analogs are more resistant to in vivo degradation in part because they are poorer substrates for both hepatic lipase and lysomal acid hydrolase.

In vivo Imaging Studies

Oil-in-water emulsions containing Compounds 3 and 7 were administered at dose levels ranging from 20 to 70 mg I/kg body weight to normal rats and tumor-bearing rats (Morris Hepatoma 7777) for CT evaluation. Tumor morphology was verified by gross pathologic inspection.

Figure 9:
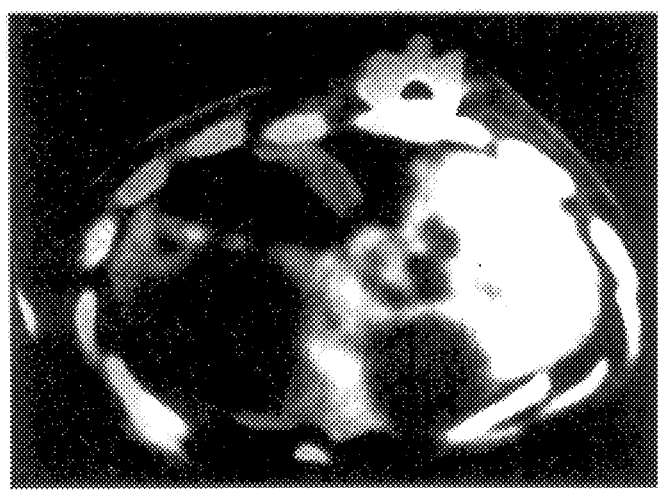
FIG. 9 is an axial CT image (3 mm slice thickness) of tumor-bearing rat (Morris Hepatoma 7777) taken one hour after administration of a CT contrast producing agent which is an oil-in-water emulsion in accordance with the present invention.

In normal rats, both compounds displayed a rapid uptake into the liver so that liver densities increased from a baseline mean of 58 HU to nearly 100 HU by 60 minutes. By 3 hours, CT density was declining for Compound 7 (DHOG), but remained high for the sterically hindered Compound 3.

composition of Example 2. Since the tumor cells are physiologically distinct from the hepatocytes, the tumor cells do not enhance and appear hypointense relative to the enhanced hepatocytes. The contrast distinction makes identification and localization of small lesions considerably easier. In this particular case, the tumors are 4 mm in diameter. FIG. 9 is an axial CT scan of another tumor-bearing rat at one hour post-administration. The presence of two tumors is clearly shown. The tumor on the left is 10 mm in diameter and the one on the right is 6 mm in diameter.

Metabolic/Elimination Studies

Figure 10:
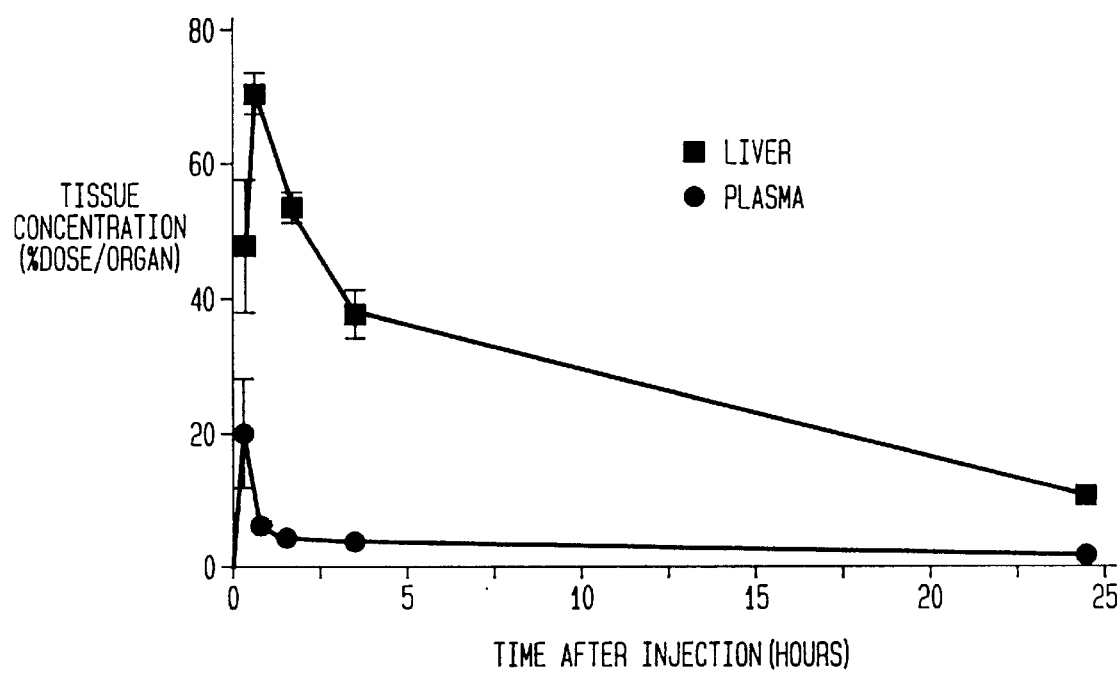
FIG. 10 is a graphic representation of the tissue biodistribution profile in liver (■) and plasma (○) expressed as tissue concentration (% administered dose per organ) as a function of time (hrs) following injection of a radioiodinated oil-in-water emulsion of the present invention.

A lipid emulsion prepared in accordance with Example 2 (10% total core lipid content) was used in the tissue distribution and elimination studies reported hereinbelow. Fasted female Sprague-Dawley rats were administered radioactive ($^{125}$I-ITG) emulsion at a dose of 25–35 mg I/kg by tail vein injection. The amount of radioactivity in 13 tissues was determined as a function of time after injection. The results are shown in FIG. 10 which is a graphic representation of the tissue biodistribution profile in liver and plasma. The tissue concentration as % administered dose per organ (mean±SEM) in liver (■) and plasma (○) are plotted as a function of time (hrs) following injection.

As shown in FIG. 10, excellent liver-selective delivery of ITG was observed in tissue distribution studies using female rats. At 30 minutes post-injection, over 65% of the total dose was accumulated in the liver. Other tissues, typically contained less that 2% of the injected dose, although the spleen did accumulate nearly 12% of the total dose. By 24 hours, less than 5% of the injected dose remained in the liver.

Figure 11:
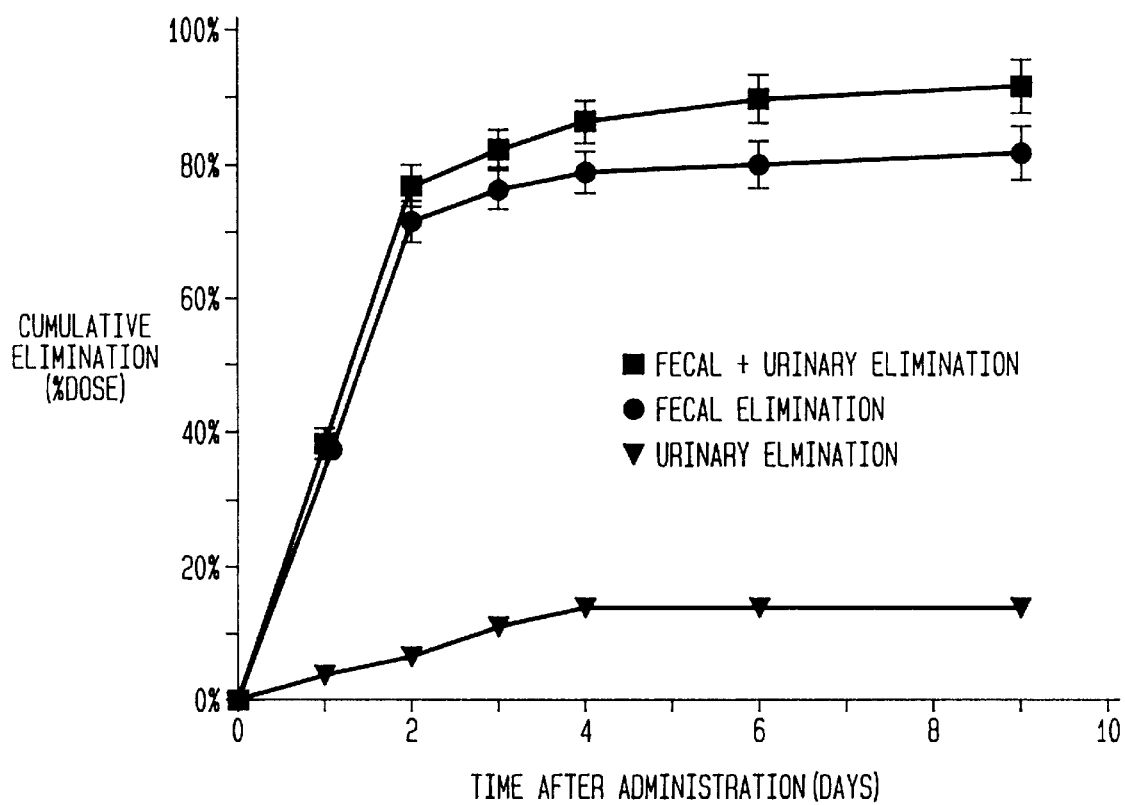
FIG. 11 is a graphic representation of the cumulative fecal and urinary elimination of radioactivity expressed as % administered dose as a function of time (hrs) following injection of a radioiodinated oil-in-water emulsion of the present invention.

Radioactive ($^{125}$I-ITG) emulsion was also administered to female rats that were subsequently placed in metabolic cages for 9 days. Feces and urine were collected daily and measured for radioactivity. The cumulative fecal and urinary elimination of radioactivity, expressed as % administered dose, is plotted as a function of time (days) following injection of the radioactive emulsion in FIG. 11. Referring to FIG. 11, the lines are marked as follows: combined fecal and urinary elimination (■), fecal elimination (●), and urinary elimination (▼).

The results from the elimination studies show that the vast majority of the ITG was metabolized by the liver and eliminated through the biliary pathway. Fecal elimination comprised just over 80% of the total elimination while urinary excretion contributed less than 20% of the elimination. In all, over 94% of the injected dose was recovered by the end of the experiment, with more than 80% being excreted by the second day.

Figure 12:
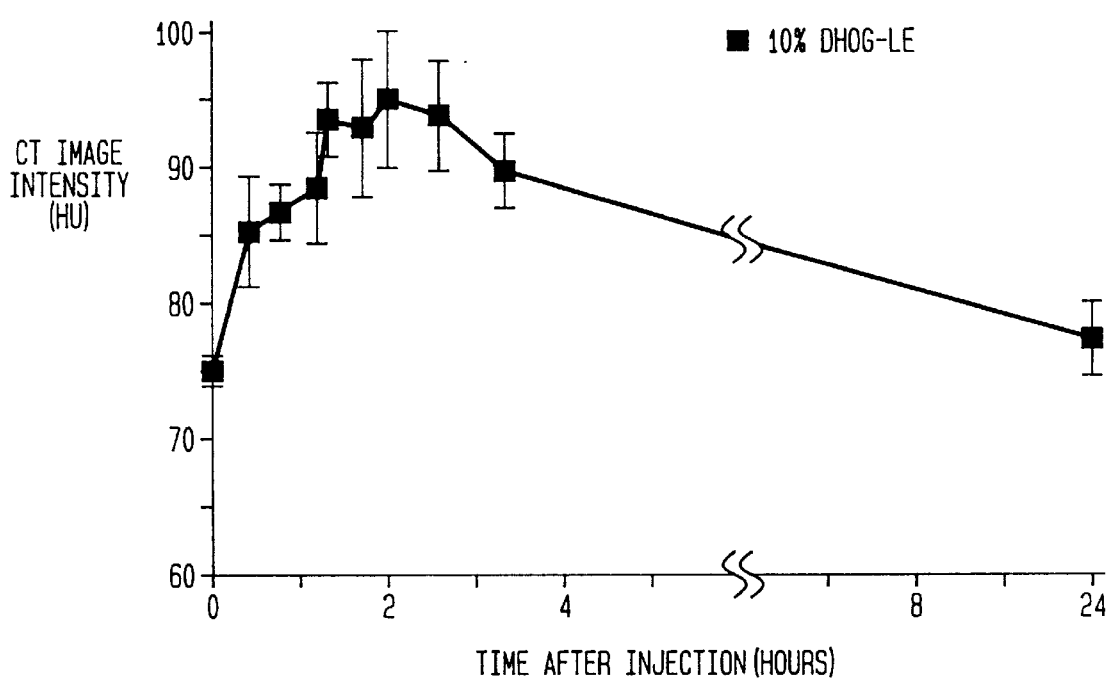
FIG. 12 is a graphic representation of CT liver intensity following intravenous bolus administration of a radioiodinated oil-in-water emulsion of the present invention expressed as image intensity in Hounsfield Units (HU) as a function of time (days) following administration.

To assess the tissue-selective CT efficacy of the oil-in-water emulsion of the present invention, a fasted female dog was imaged at various timepoints up to 24 hours after injection of a bolus dose of the emulsion of Example 2. Enhancement of the liver paralleled the tissue distribution profiles observed with rats. FIG. 12 is a graphic representation of the CT image intensity of the liver (HU) plotted as a function of time, in hours, following injection. As shown in FIG. 12, liver enhancement increased to a maximum by 60 minutes after administration and remained high for up to 2 hours. By 24 hours post-injection, however, the liver intensity had returned to pre-contrast values. The intensity of the gallbladder increased steadily with time so that by 24 hours post-injection, the CT intensity had increased by 642% over pre-contrast values. The values plotted on FIG. 12 represent the mean ±SEM of 10–15 ROI measurements from three sequential liver scans. Slice thickness for all scans was 5 mm.

Figure 13:
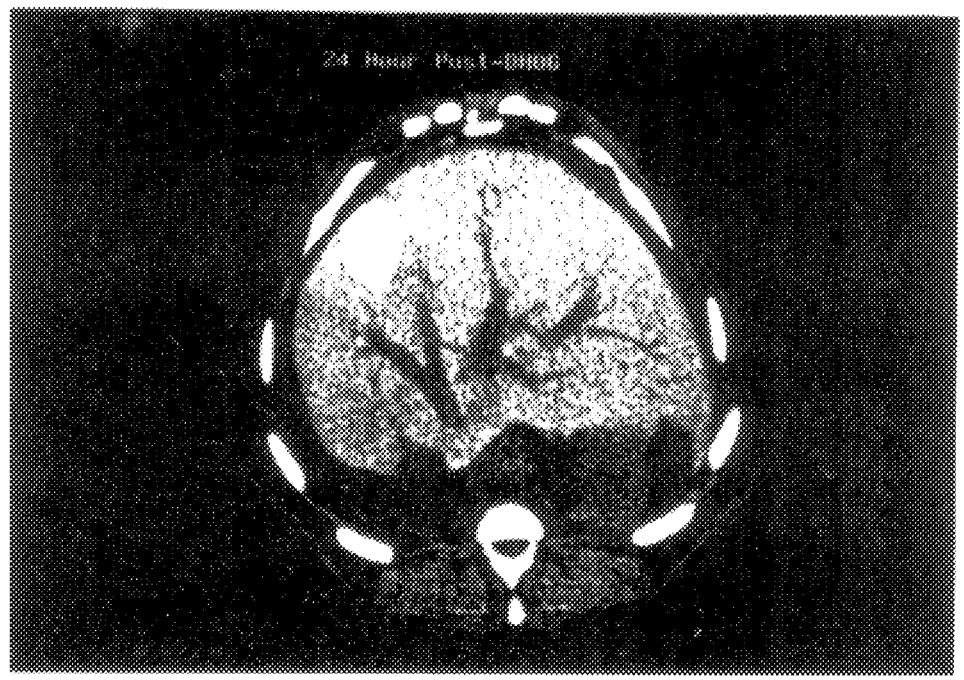
FIGS. 13 to 16 are CT images of the hepatobiliary system of a dog taken 24 hours after administration of a CT contrast agent which is an oil-in-water emulsion in accordance with the present invention.
Figure 14:
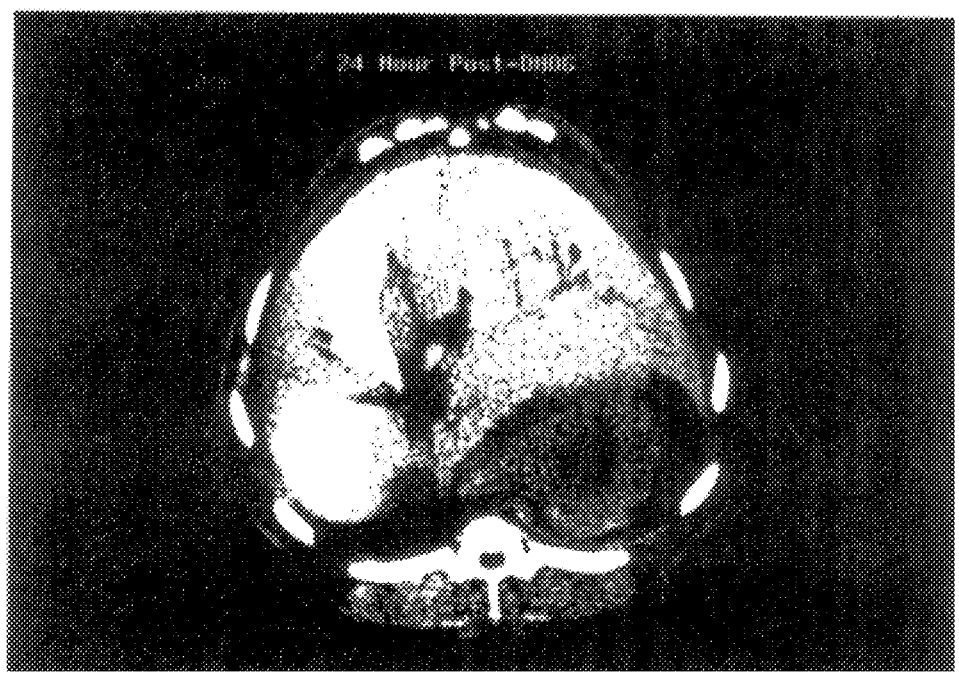
Figure 15:
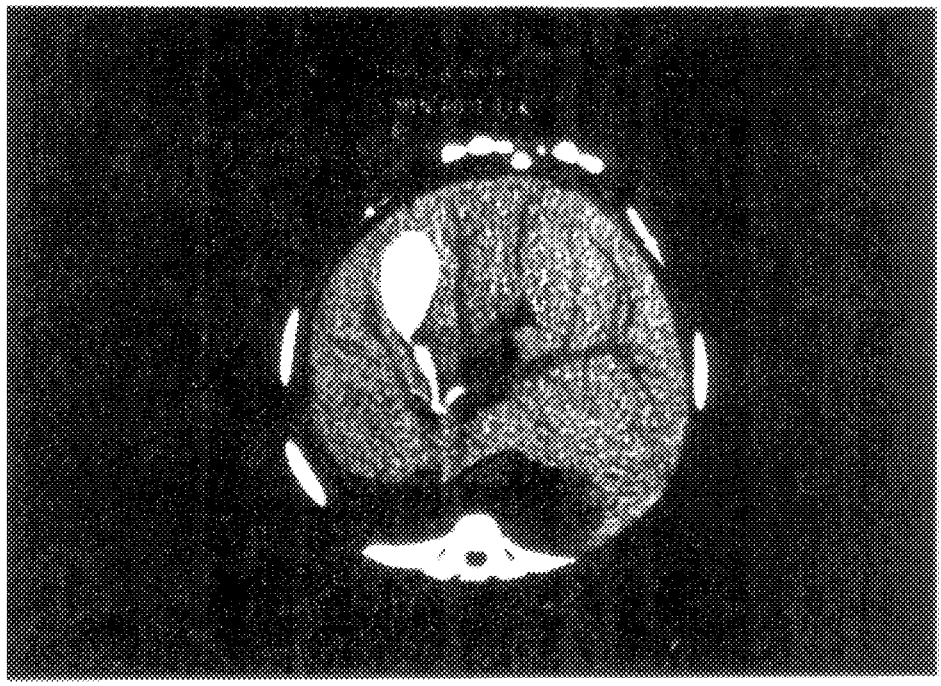
Figure 16:
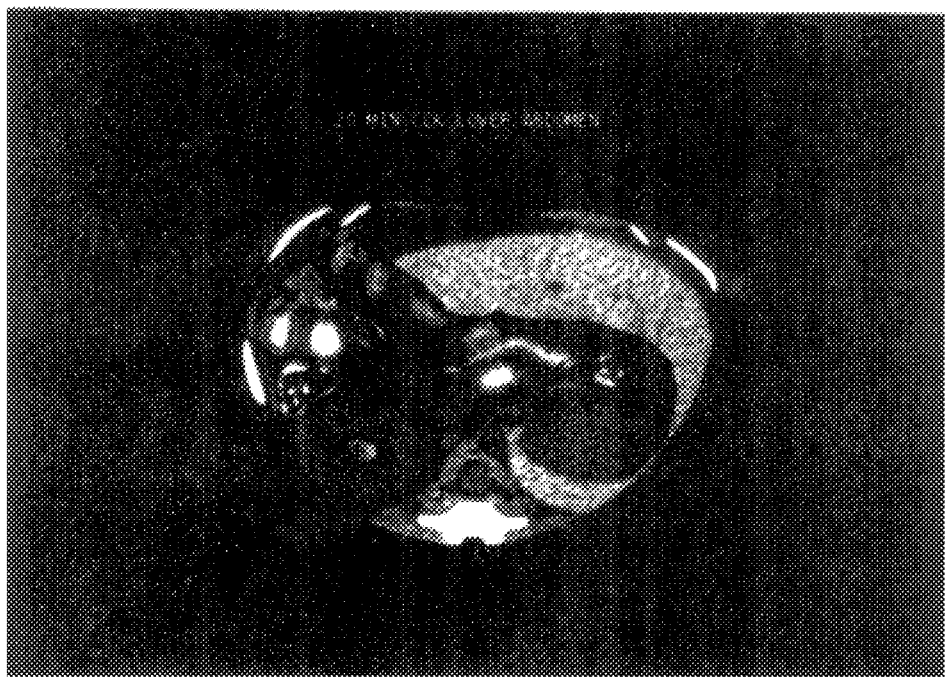

FIGS. 13 to 16 are CT images at 24 hours post-administration. Referring to FIG. 13, the gall bladder, in the upper left corner, is greatly enhanced. FIG. 14 shows an image at a lower anatomical level of the same animal at approximately the same time. The gall bladder is full and greatly enhanced. Cholecystokinin was administered to the dog to initiate emptying of the gall bladder. FIG. 15 is an image generated 5 minutes post-administration of the cholecystokinin. The cystic and common bile duct are now opacified. FIG. 16 is a lower level slice of the same dog taken 20 minutes post-administration of the cholecystokinin. The contrast enhancement is now located in the bowel. Material that is eliminated from the hepatocytes into the bile is collected and concentrated in the gall bladder. Therefore, DHOG and/or its metabolites that have been processed by the hepatocytes and eliminated in the bile will accumulate in the gallbladder. Both the liver tissue and the biliary system were enhanced on CT images following administration of DHOG in the oil-in-water lipid emulsion of the present invention.

The biodistribution studies demonstrated excellent target tissue specificity, with the vast majority of the injected dose being localized to the liver. Data from metabolic clearance studies suggest delivery of the ITG to the hepatocytes, as more than 80% of the injected dose is rapidly eliminated in the feces through the bile. The hepatocyte targeting was also confirmed in CT imaging studies, where the contents of the gallbladder showed tremendous increases in image intensity with time as ITG accumulated in the gallbladder bile.

The hepatocyte-selective nature of the emulsions of the present invention permit imaging of the hepatobiliary system. Therefore, use of the emulsions would be particularly advantageous in the diagnosis and/or treatment of any disease that alters the hepatic lipase and lysomal acid lipase activity, such as diabetes, cancer, cirrhosis, alcoholism, primary and metastatic liver tumors, hepatitis, cholecystitis, obstructive jaundice, liver transplant functional assessment, fibrotic liver, fatty liver, and many others.

EXAMPLE 4

For comparative purposes, oil-in-water emulsions were formulated using only sonication (Formulation 4a) or high speed mixing on a Polytron plus sonication (Formulation 4b). The components of Formulations 4a and 4b are as follows:

500.0 mg triolein
506.6 mg DHOG
2.40 ml of 100 mg/ml DOPC in $CHCl_3$
47.1 mg cholesterol
500.0 mg USP glycerol
11.9 mg α-tocopherol
total to 10 ml sterile water Formulation 4a:

2.40 ml of 100 mg/ml DOPC in a solvent, specifically $CHCl_3$, was added to a Corex tube. The solvent was evaporated under nitrogen until a residue formed in the bottom of the tube. 500 mg triolein were added on top of the DOPC and 47.1 mg cholesterol were added to the DOPC/TO mixture. An anti-oxidant, 11.9 mg α-tocopherol, was added after the cholesterol.

In a separate small glass vial, 506.6 mg DHOG were dissolved in peroxide-free ether and transferred quantitatively to the lipid mixture in the Corex tube. Additional ether was added to the tube to facilitate complete mixing of the lipids. The lipids were heated gently under a stream of nitrogen to drive off the ether. When most of the ether was gone, the mixture was re-suspended in a small volume of additional ether and transferred to a gas-tight Hamilton syringe. The Corex tube was rinsed with ether and the volume was added to the contents of the syringe. About 5 ml total volume was obtained, 2 ml of which was the actual lipid component.

The syringe was arranged in a syringe pump set to deliver the contents at a constant rate of 0.57 ml/min. Approximately 5.0 ml of anhydrous glycerol in sterile water were placed in a stoppered glass vial and a magnetic stir bar was used to mix the solution on a heating plate. When the temperature of the aqueous glycerol solution was 37° to 40° C., the lipids were added to the vial through a polyethylene tube. The vial was vented with a needle and exposed to a stream of nitrogen gas. At the specified flow rate of 0.57 ml/min, addition of the lipids took about 10 minutes. Constant stirring formed a crude emulsion. The tubing from the syringe was removed after all traces of ether were gone and the vial was sealed under nitrogen. The sealed emulsion was allowed to mix under constant, vigorous stirring for 1 hour at 37° to 40° C.

The crude emulsion was removed from the vial into a gas-tight syringe and the vial was rinsed twice with a small volume of anhydrous glycerol. The emulsion and the washes were combined in the syringe. Anhydrous glycerol was added to obtain a final volume of 10.0 ml and the emulsion was mixed by inversion directly in the syringe.

The emulsion was separated into two separate and equal aliquots of 5 ml apiece. One of the 5 ml aliquots was subjected to emulsification by sonication. The crude emulsion was placed in a water bath at room temperature into which the horn of the sonicator was immersed. The sonicator was set to run in continuous mode for 5 minutes at an output setting of 6. This setting resulted in a power output of 70–80% on the needle dial of the sonicator. The emulsion was collected and stored in a glass-stoppered vial under nitrogen.

Formulation 4b:

The second 5 ml aliquot of crude emulsion was processed into a final emulsion by homogenization with a Polytron homogenizer. The emulsion was placed in a glass Corex tube and homogenized, under nitrogen, for 5 minutes at 25,000 rpm with a small volume Polytron generator.

EXAMPLE 5

An oil-in-water emulsion of the following composition was made using the formulation method of Example 2:

800 mg triolein
200 mg DHOG
120 mg egg phosphatide
10 mg cholesterol
225 mg glycerol
total volume to 10 ml with 0.9% saline 1.20 ml of 100 mg/ml egg phosphatide was added to a 50 ml glass tube. The solvent was evaporated under partial vacuum at 40° C. for about 45 minutes on a rotary evaporator until the solvent was removed. The tube was removed from the rotary evaporator and 800 mg triolein were added on top of the egg phosphatide. 10 mg cholesterol were then added to the DOPC/TO mixture. Next, 200 mg DHOG were added to the lipid mixture. Finally, about 3 ml $CHCl_3$ were added to the tube to facilitate complete mixing of the lipids.

The lipids were mixed by agitation and an additional 1 ml of $CHCl_3$ was added to rinse material from the walls of the tube. The lipid mixture was returned to the rotary evaporator to remove the $CHCl_3$ under vacuum at 40° C. When the bulk of the solvent had been removed, the vacuum source was switched to a direct drive vacuum pump for an additional 45 minutes. The tube was then transferred from the rotary evaporator to a high vacuum line for another 1.5 hours. The tube was sealed, flushed with nitrogen, and stored overnight at 8° C.

The tube and contents were warmed to 37° C. and connected to the high vacuum system to remove the final traces of solvent. A 225.6 mg aliquot of glycerol was then added to the lipid mixture and the components were processed on the Polytron under a stream of nitrogen. Initial emulsification of this mixture was done at 12,500 rpm for 5 minutes at less than 55° C. followed by the slow addition of the aqueous phase. After the water was added, the emulsion was processed for 5 minutes at 25,000 rpm using the standard Polytron generator. The emulsion was rinsed from the generator with a small volume of sterile water and the contents were transferred to a gas-tight syringe. A final volume of 10.0 ml emulsion was obtained by the addition of water.

The emulsion was transferred to the MicroFluidizer 110S sample reservoir and the emulsion was processed for 10 minutes at 14,700 psi using the continuous pass mode. Processed emulsion was collected from the unit, filtered through a sterile 0.45 μm Acrodisc filter and then filtered through a 0.22 μm Acrodisc sterile filter directly into a sterile glass multidose vial. The vial was stored under nitrogen.

EXAMPLE 6

Cholesterol not only helps to stabilize the monolayer to resist changes in diameter over time following heat sterilization, but facilitates the association of the emulsion with the apoproteins required for targeting the emulsion to hepatocytes, particularly Apo E. Most importantly, however, emulsions made in accordance with the present invention will retain the ability to associate with apo E after heat sterilization as shown in Table 3 below. Emulsions formulated in Examples 2 to 5 were incubated in lipoprotein-deficient plasma and re-isolated. Lowry assay was used to determine the μg protein per ml emulsion since the amount of protein includes association with Apo AI and Apo AIV. Samples of the emulsions of Example 2 and Example 5 were subjected to standard autoclaving and assayed for mean particle diameter.

TABLE 3

| Emulsion Formula | Initial Size NI/NN | Size Stability | Stable to Autoclave | μg protein per ml emulsion | Apolipoprotein | | | |
|---|---|---|---|---|---|---|---|---|
| | | | | | AI | AIV | E | C |
| Ex. 4a | 4.0–7.8 μm/182 nm | YES | NO | 3 | – | ++ | – | – |
| Ex. 4b | 350–764 nm/40–42 nm | YES | YES | 28 | + | ++ | – | – |
| Ex. 5 | 213 nm/77 nm | YES | NO | 65 | ++ | +++ | + | – |
| Ex. 2 | 245 nm/80 nm | YES | YES | 78 | ++ | +++ | + | – |
| Ex. 5 autoclave | 6 μm/2.4 μm | YES | | 52 | – | – | – | – |
| Ex. 2 Autoclave | 272 nm/114 nm | YES | | 70 | +++ | +++ | + | – |

*C is Apo C II and C III
Key:
– = not present
+ = present, low level
++ = present, medium level
+++ = present, high level

EXAMPLE 7

In another specific illustrative embodiment, DHOG (Compound 7 on Table 1 in Example 1) was formulated into an oil-in-water emulsion having 20% total core lipid content for use as a hepatocyte-selective CT agent. The general formula is was follows:

20% (w/v) Total Lipid Triolein (TO)+DHOG TO:DHOG (w/w)=1:1
3.6% (w/v) phospholipid DOPC
0.5% (w/v) % cholesterol Cholesterol:DOPC (molar ratio)=0.4

5% (w/v) USP glycerol 0.6% (w/v) α-tocopherol sterile water as bulk aqueous phase In terms of actual quantities:

| | |
|---|---|
| DHOG | 1000.3 mg |
| triolein | 1002.7 mg |
| cholesterol | 71.1 mg |
| α-tocopherol | 61.2 mg |
| DOPC | 360 mg |
| glycerol | 500.7 mg |
| sterile water | 7.40 ml |

The lipid core components were dissolved in a solvent which was subsequently removed as set forth above in Example 2. USP glycerol was combined with the lipid mixture and emulsified under nitrogen for 5 minutes on the Polytron at 12,500 rpm. A 5.5 ml aliquot of sterile water was added and emulsification was continued at 25,000 rpm for 5 minutes at <55° C. The rough emulsion and generator rinse were combined and adjusted to 10 ml with sterile water prior to final emulsification in the MicroFluidizer, Model 110-S, for 10 minutes at 14,700 psi between 34.4–35.4° C. The emulsion was then passed through sterile filters of 0.45 pm and 0.2 pm pore size into a sterile multidose vial.

EXAMPLE 8

In yet another specific embodiment, DBOG (Compound 4 on Table 1 in Example 1) was formulated into an oil-in-water emulsion having 20% total core lipid content, 3.6% DOPC, and a molar ratio of cholesterol to DOPC of 0.27. The general formula is as follows:

| | |
|---|---|
| DBOG | 1000.5 mg |
| triolein | 1004.3 mg |
| cholesterol | 47.5 mg |
| α-tocopherol | 66.2 mg |
| DOPC | 360 mg |
| glycerol | 502.6 mg |
| sterile water | 7.4 ml |

The oil-in-water emulsion was processed was under the same conditions described in Example 7.

EXAMPLE 9

Figure 17:
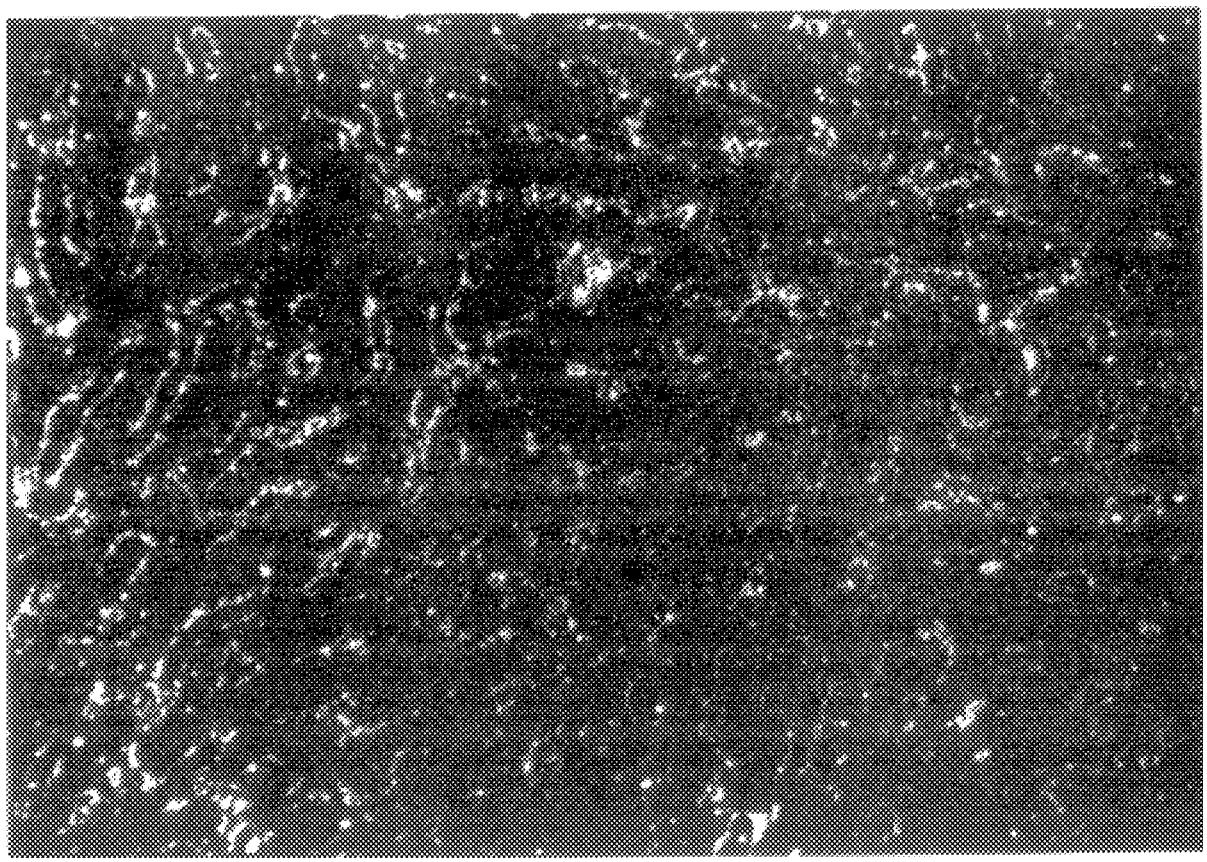
FIGS. 17 and 18 are microscopic autoradiographs of liver tissue of a control animal and a test animal at 3 hours post-injection of a vehicle (control) or an oil-in-water emulsion containing a radioiodinated triglyceride in accordance with the present invention.
Figure 18:
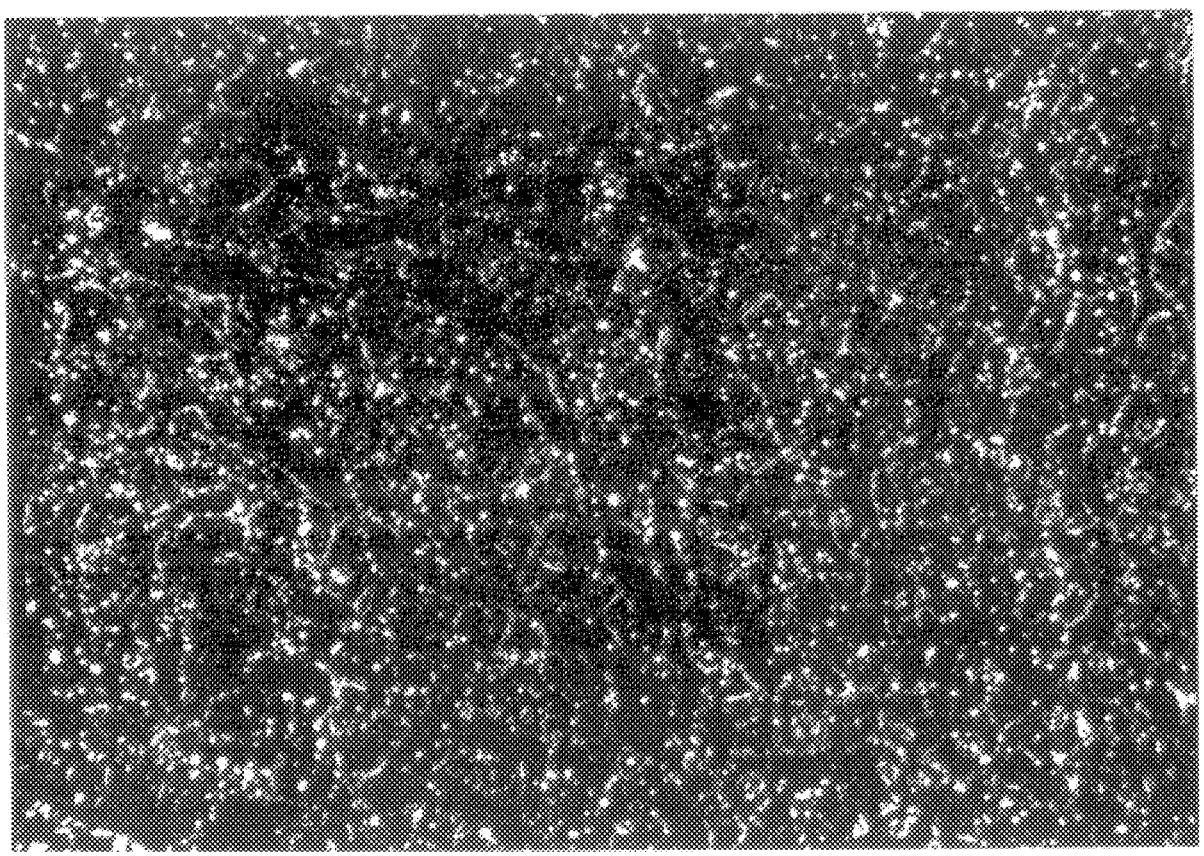

FIGS. 17 and 18 are photomicroscopic autoradiographs of liver tissue of a control animal and a test animal, respectively. The autoradiographs were taken following injection of a TO emulsion (control) or an oil-in-water emulsion of the present invention (test) into a live animal, a three hour biodistribution period, and a subsequent liver perfusion and fixation process. The test oil-in-water emulsion used to obtain the autoradiographic image of FIG. 18 contained 10% w/v total lipid core content which was 5% radioiodinated 2-oleoylglycerol-1,3-bis[iopanoate](DIOG or Compound 3 from Table 1) and 5% TO in a formulation similar to Example 2. The control emulsion contained 10% w/v TO in the lipid core and was used to assess whether the emulsion per se would cause morphologic damage to liver tissue.

FIG. 17 shows only the normal background radioactivity found in living tissue and exhibits no morphologic damage. FIG. 18 shows hepatocyte-selective delivery of the oil-in-water emulsion of the present invention, i.e., intracellular localization of the iodinated triglyceride. Referring to FIG. 18, grains of radioactivity associated with the iodinated triglyceride were mainly present within the morphological boundaries of hepatocytes as opposed to being localized at the surface of the cell, located in liver sinusoidal spaces, or located in Kupffer cells. As such, the results of this autoradiographic study support the conclusion that the oil-in-water emulsion of the present invention delivers its contents primarily to the hepatocytes. Furthermore, the liver tissue of FIG. 18 exhibits no morphologic damage from the administration of the oil-in-water emulsion of the present invention.

EXAMPLE 10

Comparative Studies of Emulsions Comprising Pure Components Versus Natural

In vivo CT imaging studies were conducted using soybean oil/egg phosphatide-based formulations and triolein/DOPC-based formulations in order to assess the relative advantages of the use of pure, synthetic compounds in the oil-in-water emulsions of the present invention. Preliminary CT studies showed that soybean oil/egg phosphatide formulations performed essentially equally. However, CT imaging cannot directly distinguish between material delivered to the hepatocytes and material delivered to the Kuppfer cells.

If evaluation of liver function is desired, however, a contrast agent must be delivered to the hepatocytes, and not to the Kuppfer cells or other cells of the liver. With targeted delivery to the hepatocytes, the relative differences in initial enhancement of the liver, and subsequent clearance of the enhancement agent from the liver, can be observed by CT imaging and correlated to metabolic function. The biodistribution and elimination studies presented hereinbelow demonstrate that the soybean oil/egg phosphatide-based formulations are not directed to the hepatocytes in the same manner as are the triolein/DOPC-based formulations of the present invention.

Tissue biodistribution studies were conducted to evaluate iodinated triglyceride localization profiles with soybean oil/egg phosphatide formulations as compared to triolein/DOPC formulations. The soybean oil/egg phosphatide formulation was chosen to simulate a typical prior art parenteral nutrition supplement such as Liposyn (Abbott Laboratories, North Chicago, Ill.) or Intralipid (Kabivitrum AB, Stockholm, Sweden). The composition of the soybean oil/egg phosphatide formulation used in the studies of Example 10 was as follows:

| | |
|---|---|
| DHOG | 500 mg |
| soybean oil | 500 mg |
| egg phosphatide | 120 mg |
| glycerol | 250 mg |
| sterile water | to 10 ml final volume |

An oil-in-water emulsion of the soybean oil/egg phosphatide was processed in a manner analogous to Example 2. The triolein/DOPC formulation used in this study was identical to Example 2. Both emulsions were formulated with a tracer amount of radiolabeled ITG and subsequently administered to fasted female rats at a dose of 24–26 mg I/kg. The animals were sacrificed at various time points (30 minutes, 3 hours, 24 hours) and 13 tissues were assayed for radioactivity. The results for the soybean oil/egg phosphatide formulation are shown below in Tables 4A to 4C. The results for the triolein/DOPC formulation (Example 2) are shown below in Tables 4D to 4F.

TABLE 4A

30 Minutes:
10% DHOG Soybean Oil/Egg Phosphalide-LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 16.250 | 1.898 | 0.283 | 0.040 | 0.057 | 0.007 | 0.015 | 0.002 |
| Blood | 6.919 | 0.656 | 0.119 | 0.008 | 0.024 | 0.002 | 1.208 | 0.114 |
| Bone Marrow | 23.141 | 2.188 | 0.400 | 0.038 | 0.082 | 0.008 | 0.283 | 0.027 |
| Fat | 9.209 | 3.070 | 0.157 | 0.049 | 0.032 | 0.011 | 2.299 | 0.766 |
| Heart | 136.451 | 10.779 | 2.374 | 0.252 | 0.481 | 0.038 | 1.391 | 0.110 |
| Kidney | 5.122 | 0.120 | 0.089 | 0.002 | 0.018 | 0.000 | 0.137 | 0.003 |
| Liver | 653.371 | 23.129 | 11.296 | 0.275 | 2.304 | 0.082 | 75.842 | 0.667 |
| Lung | 78.456 | 13.129 | 1.357 | 0.232 | 0.277 | 0.046 | 1.549 | 0.260 |
| Muscle | 1.735 | 0.217 | 0.030 | 0.003 | 0.006 | 0.001 | 2.784 | 0.348 |
| Ovary | 7.939 | 2.651 | 0.138 | 0.047 | 0.028 | 0.009 | 0.010 | 0.003 |
| Plasma | 8.211 | 0.536 | 0.142 | 0.005 | 0.029 | 0.002 | 0.788 | 0.051 |
| Spleen | 440.404 | 111.704 | 7.515 | 1.687 | 1.553 | 0.394 | 3.715 | 0.872 |
| Thyroid | 29.459 | 7.809 | 0.507 | 0.134 | 0.104 | 0.028 | 0.008 | 0.002 |

TABLE 4B 3 hours:
10% DHOG Soybean Oil/Egg Phosphalide-LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 7.705 | 1.650 | 0.139 | 0.031 | 0.027 | 0.006 | 0.007 | 0.001 |
| Blood | 10.234 | 0.519 | 0.184 | 0.009 | 0.036 | 0.002 | 1.786 | 0.091 |
| Bone Marrow | 12.887 | 1.699 | 0.232 | 0.032 | 0.045 | 0.006 | 0.157 | 0.021 |
| Fat | 5.100 | 0.801 | 0.091 | 0.013 | 0.018 | 0.003 | 1.273 | 0.201 |
| Heart | 101.935 | 13.810 | 1.831 | 0.249 | 0.359 | 0.049 | 1.038 | 0.141 |
| Kidney | 11.143 | 1.017 | 0.200 | 0.016 | 0.039 | 0.004 | 0.299 | 0.027 |
| Liver | 545.082 | 23.030 | 9.781 | 0.316 | 1.922 | 0.082 | 65.162 | 2.560 |
| Lung | 49.854 | 6.725 | 0.893 | 0.110 | 0.176 | 0.024 | 0.984 | 0.133 |
| Muscle | 1.866 | 0.336 | 0.033 | 0.006 | 0.007 | 0.001 | 2.994 | 0.539 |
| Ovary | 4.617 | 0.252 | 0.083 | 0.005 | 0.016 | 0.001 | 0.006 | 0.000 |
| Plasma | 10.039 | 0.752 | 0.180 | 0.014 | 0.035 | 0.003 | 0.963 | 0.072 |
| Spleen | 290.358 | 49.155 | 5.233 | 0.926 | 1.023 | 0.173 | 2.768 | 0.322 |
| Thyroid | 163.598 | 45.812 | 2.952 | 0.858 | 0.577 | 0.161 | 0.043 | 0.012 |

TABLE 4C 24 hours:
10% DHOG Soybean Oil/Egg Phosphatide-LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 4.844 | 0.506 | 0.103 | 0.011 | 0.021 | 0.002 | 0.005 | 0.001 |
| Blood | 6.210 | 1.018 | 0.131 | 0.021 | 0.027 | 0.004 | 1.346 | 0.220 |
| Bone Marrow | 9.066 | 3.160 | 0.193 | 0.069 | 0.040 | 0.014 | 0.138 | 0.048 |
| Fat | 4.367 | 0.525 | 0.093 | 0.012 | 0.019 | 0.002 | 1.354 | 0.163 |
| Heart | 10.300 | 2.620 | 0.219 | 0.058 | 0.045 | 0.011 | 0.130 | 0.033 |
| Kidney | 10.659 | 0.677 | 0.226 | 0.016 | 0.047 | 0.003 | 0.355 | 0.023 |
| Liver | 195.966 | 33.186 | 4.142 | 0.684 | 0.858 | 0.145 | 33.451 | 4.592 |
| Lung | 19.644 | 1.547 | 0.415 | 0.027 | 0.086 | 0.007 | 0.482 | 0.037 |
| Muscle | 0.992 | 0.090 | 0.021 | 0.002 | 0.004 | 0.000 | 1.976 | 0.178 |
| Ovary | 3.151 | 0.076 | 0.067 | 0.002 | 0.014 | 0.000 | 0.005 | 0.000 |
| Plasma | 5.862 | 0.937 | 0.124 | 0.019 | 0.026 | 0.004 | 0.698 | 0.111 |
| Spleen | 93.235 | 25.380 | 1.962 | 0.509 | 0.408 | 0.111 | 0.870 | 0.198 |
| Thyroid | 466.549 | 38.884 | 9.860 | 0.733 | 2.043 | 0.168 | 0.153 | 0.013 |

TABLE 4D

30 Minutes:
10% DHOG-TO/DPOC LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 278.662 | 77.937 | 3.228 | 0.903 | 0.709 | 0.202 | 0.181 | 0.051 |
| Blood | 31.525 | 5.414 | 0.365 | 0.063 | 0.080 | 0.014 | 3.962 | 0.708 |
| Bone Marrow | 29.753 | 2.206 | 0.345 | 0.026 | 0.075 | 0.006 | 0.261 | 0.019 |
| Fat | 9.657 | 0.691 | 0.112 | 0.008 | 0.024 | 0.002 | 1.731 | 0.118 |
| Hear | 89.151 | 8.516 | 1.033 | 0.099 | 0.226 | 0.022 | 0.653 | 0.065 |
| Kidney | 11.440 | 0.590 | 0.132 | 0.007 | 0.029 | 0.001 | 0.220 | 0.011 |
| Liver | 776.875 | 44.460 | 8.998 | 0.515 | 1.966 | 0.095 | 62.083 | 2.950 |
| Lung | 70.810 | 4.768 | 0.820 | 0.055 | 0.179 | 0.012 | 1.004 | 0.066 |
| Muscle | 3.003 | 0.195 | 0.035 | 0.002 | 0.008 | 0.000 | 3.461 | 0.225 |
| Ovary | 20.441 | 3.032 | 0.237 | 0.035 | 0.052 | 0.008 | 0.018 | 0.003 |
| Plasma | 43.216 | 8.366 | 0.501 | 0.097 | 0.110 | 0.022 | 2.985 | 0.598 |
| Spleen | 2446.667 | 265.950 | 28.338 | 3.080 | 6.206 | 0.714 | 15.876 | 1.622 |
| Thyroid | 95.207 | 22.890 | 1.103 | 0.265 | 0.240 | 0.056 | 0.018 | 0.004 |

TABLE 4E 3 hours:
10% DHOG-TO/DPOC LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 60.237 | 9.900 | 0.704 | 0.134 | 0.152 | 0.025 | 0.039 | 0.006 |
| Blood | 29.681 | 2.452 | 0.344 | 0.025 | 0.075 | 0.007 | 3.717 | 0.322 |
| Bone Marrow | 24.467 | 6.187 | 0.280 | 0.064 | 0.062 | 0.016 | 0.215 | 0.055 |
| Fat | 8.610 | 1.091 | 0.099 | 0.010 | 0.022 | 0.003 | 1.543 | 0.202 |
| Heart | 44.156 | 12.434 | 0.509 | 0.135 | 0.112 | 0.032 | 0.323 | 0.092 |
| Kidney | 21.658 | 0.540 | 0.251 | 0.001 | 0.055 | 0.002 | 0.416 | 0.012 |
| Liver | 485.278 | 54.873 | 5.623 | 0.629 | 1.226 | 0.135 | 37.574 | 3.887 |
| Lung | 44.880 | 0.558 | 0.521 | 0.017 | 0.113 | 0.002 | 0.636 | 0.009 |
| Muscle | 2.945 | 0.348 | 0.034 | 0.003 | 0.007 | 0.001 | 3.391 | 0.415 |
| Ovary | 20.164 | 5.997 | 0.231 | 0.064 | 0.051 | 0.015 | 0.018 | 0.005 |
| Plasma | 24.940 | 3.993 | 0.287 | 0.039 | 0.063 | 0.010 | 1.717 | 0.282 |
| Spleen | 1437.084 | 76.326 | 16.646 | 0.775 | 3.635 | 0.208 | 8.724 | 0.613 |
| Thyroid | 266.971 | 66.535 | 3.116 | 0.831 | 0.675 | 0.169 | 0.051 | 0.013 |

TABLE 4F 24 hours:
10% DHOG-TO/DPOC LE

| Tissue | Mean dpm/mg | SEM | Mean % dose/g | SEM | Mean kg dose/g | SEM | Mean % dose/organ | SEM |
|---|---|---|---|---|---|---|---|---|
| Adrenal | 6.893 | 1.857 | 0.162 | 0.043 | 0.035 | 0.009 | 0.009 | 0.002 |
| Blood | 6.207 | 3.675 | 0.148 | 0.089 | 0.031 | 0.018 | 1.544 | 0.913 |
| Bone Marrow | 3.611 | 0.354 | 0.085 | 0.009 | 0.018 | 0.002 | 0.063 | 0.006 |
| Fat | 2.489 | 0.474 | 0.059 | 0.011 | 0.013 | 0.002 | 0.887 | 0.172 |
| Heart | 4.226 | 0.891 | 0.100 | 0.022 | 0.021 | 0.005 | 0.061 | 0.013 |
| Kidney | 5.065 | 0.277 | 0.120 | 0.008 | 0.025 | 0.001 | 0.194 | 0.011 |
| Liver | 54.295 | 6.663 | 1.282 | 0.165 | 0.273 | 0.033 | 14.077 | 0.739 |
| Lung | 7.053 | 1.588 | 0.167 | 0.038 | 0.035 | 0.008 | 0.198 | 0.044 |
| Muscle | 0.635 | 0.059 | 0.015 | 0.001 | 0.003 | 0.000 | 1.453 | 0.140 |
| Ovary | 2.592 | 0.200 | 0.061 | 0.006 | 0.013 | 0.001 | 0.005 | 0.000 |
| Plasma | 2.396 | 0.108 | 0.056 | 0.002 | 0.012 | 0.001 | 0.328 | 0.016 |
| Spleen | 111.586 | 15.137 | 2.628 | 0.345 | 0.561 | 0.074 | 1.510 | 0.136 |
| Thyroid | 579.753 | 109.374 | 13.738 | 2.770 | 2.916 | 0.550 | 0.219 | 0.041 |

Referring to Table 4A, the average accumulation of iodinated triglyceride in the liver, at 30 minutes post-injection, was 76% of the injected dose per organ. Less than 4% of the total dose was present in the spleen, and the blood contained less than 2% of the injected dose. All other tissues accumulated less that 2.5% of the administered dose.

However, at 3 hours post-injection (Table 4B), the iodinated triglyceride delivered in the soybean oil/egg phosphatide emulsion had failed to clear appreciably from the liver, i.e., greater than 65% of the injected dose remained in the liver at this time point. On the other hand, as shown on Table 4E, only 35% of the injected dose delivered by the TO/DOPC emulsion remained in the liver.

This distinction in kinetic biodistribution profile may be explained by the fact that the majority of the iodinated triglyceride delivered in the soybean oil/egg phosphatide emulsion was delivered to the RES cells rather than the hepatocytes. If the radioactive material was delivered to the Kupffer cells, following first pass clearance the imaging and biodistribution profiles would, at early timepoints show excellent liver localization. However, with time, the material would not be cleared from the liver nearly as quickly as if it had been delivered to the hepatocytes. A comparison of Table 4C with Table 4F demonstrates that the TO/DOPC emulsion cleared from the liver quicker than the soybean oil/egg phosphatide emulsion.

In addition, Folch lipid extraction analysis of liver and plasma samples provided information about the form of the iodinated triglyceride-derived radioactivity in each respective sample.

TABLE 5

| Time After Injection (Hours) | Mean Aqueous Conc. (% of Total) | Mean Organic Conc. (% of Total) | Mean ppt. Conc. (% of Total) |
|---|---|---|---|
| Liver | | | |
| 0.5 | 0.72% ± 0.11% | 85.04% ± 1.49% | 13.35% ± 1.56% |
| 3.0 | 1.8% ± 0.21% | 88.52% ± 0.42% | 10.40% ± 0.22% |
| Plasma | | | |
| 0.5 | 24.96% ± 2.24% | 57.88% ± 2.21% | 17.16% ± 1.61% |
| 3.0 | 15.37% ± 1.91% | 54.94% ± 1.55% | 19.6% ± 1.46% |

The data in Table 5 confirm that there is a difference in the manner in which the two formulations were metabolized. At both 30 minutes and 3 hours post-injection, an average of 1% of all liver-associated radioactivity was water soluble, 12% was protein-associated, and 87% was organic soluble. Thus, the vast majority of liver-associated triglyceride was most likely the parent triglyceride. Results for the TO/DOPC emulsion were similar. However, in the plasma, there was no indication that metabolism of the iodinated triglyceride delivered with the soy oil/egg phosphatide formulation occurred over time, in other words, the majority of radioactivity in the plasma (62% of the total dose) was still organic soluble both 30 minutes and 3 hours after administration. On the other hand, the ITG delivered in the TO/DOPC emulsion exhibited a shift over time from being localized in the organic soluble fraction to being localized in the protein-associated and water-soluble fractions.

Figure 19:
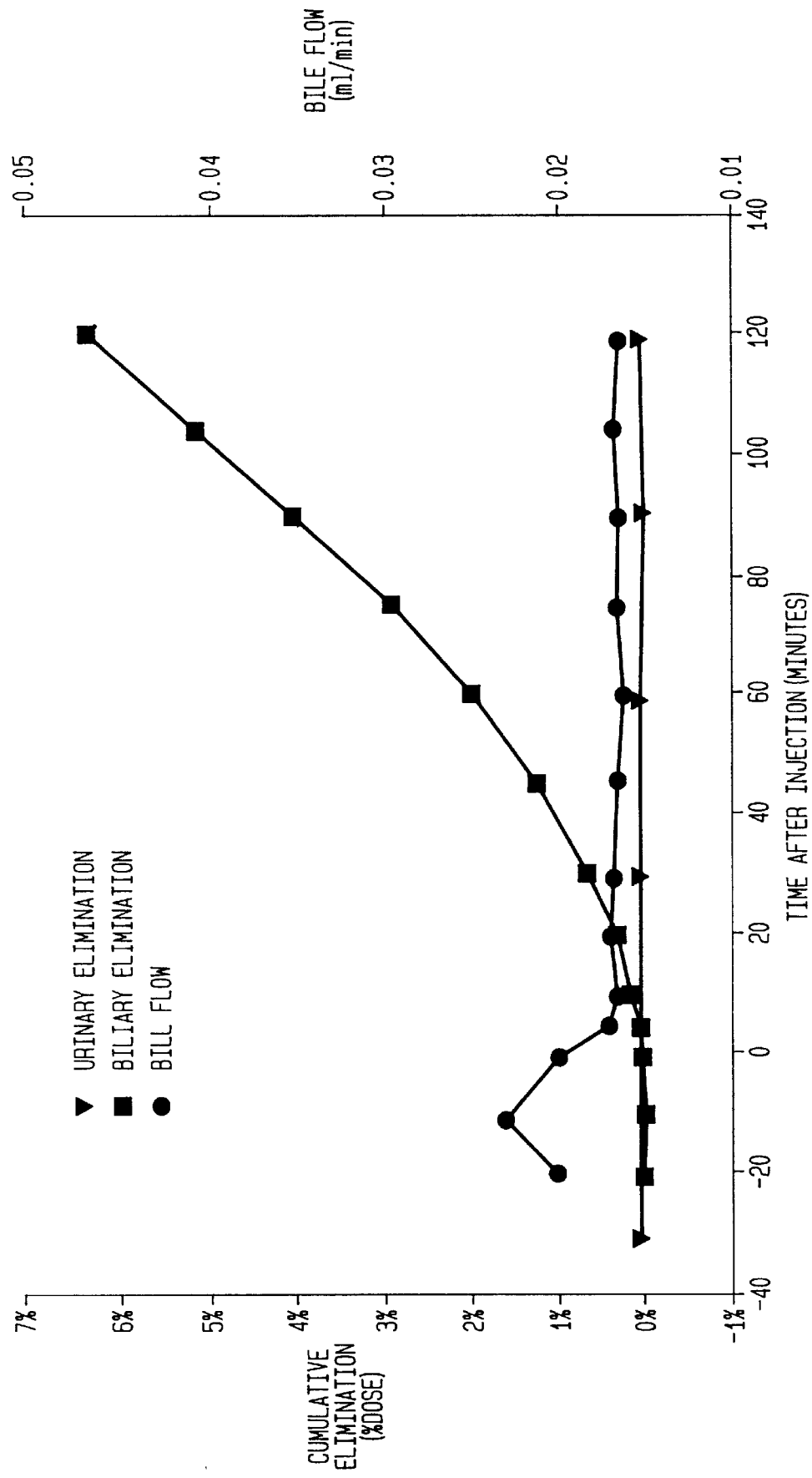
FIG. 19 is a graphic representation of the elimination profile for a radioiodinated oil-in-water emulsion and/or its metabolites obtained by direct cannulation of the bile duct and ureters of another rats expressed as cumulative elimination (% dose) for biliary elimination (■) and urinary elimination (▼) and bile flow (●; ml/min) as a function of time (mins) following injection the radioiodinated oil-in-water emulsion of the present invention.

In addition to the foregoing, biliary and urinary elimination was studied by direct cannulation of the bile duct and ureters in rats to which the radiolabeled emulsion of Example 2 was administered (27.8 mg I/kg body weight). This technique enabled bile and urine to be collected directly and continuously for up to 3 hours after administration of the test compound. The relative contributions of the biliary and urinary pathways to overall elimination of the compounds were measured. The results are reported in FIG. 19 which is a graphic representation of the elimination profile of the composition of Example 2 wherein cumulative elimination (% dose) via the biliary route (■) and the urinary route (▼), and bile flow in ml/min (●), are shown as a function of time (mins) following injection the radioiodinated oil-in-water emulsion. The majority of the iodinated triglyceride was eliminated by the biliary route, thus providing further evidence that the iodinated triglyceride had been delivered primarily to the hepatocytes.

Fluorine Embodiments:

Non-proton magnetic resonance imaging of the liver has been accomplished in the prior art with emulsified perfluorocarbons, such as Fluosol and perfluoroctylbromide, which are sequestered not only by hepatic Kupffer cells but also by reticuloendothelial cells of the spleen and bone marrow. In illustrative embodiments of the present invention, symmetrically substituted polyfluorinated triglycerides have been incorporated into chylomicron-like microemulsions as useful as magnetic resonance contrast agents.

EXAMPLE 11

In a specific illustrative embodiment, an oil-in-water emulsion contains a fluorinated triglyceride (FTG) which is glyceryl-2-oleoyl-1,3-bis(trifluoromethyl)phenyl acetate. The oil-in-water emulsion contains 10% total core lipids, 2.4% DOPC, and has a cholesterol to DOPC ratio of 0.4.

| | Quantity | Percent (w/v) |
|---|---|---|
| FTG | 670.9 mg | 6.7% |
| Triolein | 330.3 mg | 3.3% |
| Cholesterol | 47.2 mg | 0.5% |
| α-Tocopherol | 61.0 mg | 0.6% |
| DOPC | 240.0 mg | 2.4% |
| Glycerol | 500.7 mg | 5.0% |
| Sterile Water | 8.6 ml | |

The core lipids were combined and dissolved in ethyl acetate:ethanol (2:1, v/v) and then placed on a rotary evaporator to remove the solvent mixture under vacuum. After addition of glycerol to the lipid mixture, emulsification was performed in the manner described in Example 2 to afford the finished oil-in-water emulsion.

EXAMPLE 12

In another specific example, fluorinated compounds of the type shown in U.S. Pat. Nos. 5,116,599 and 5,234,680 can be incorporated in an oil-in-water emulsion of the present invention. Specifically, the lipid core components may include a fluorine-containing lipid, such as an ester or triglyceride of a perfluoro-t-butyl-containing fatty acid compounds, such as 7,7,7-trifluoro-6,6-bis (trifluoromethyl)-heptanoic acid or 8,8,8-trifluoro-7,7-bis(trifluoromethyl)-octanoic acid.

The oil-in-water emulsions of the present invention are suitable for parenteral administration to a mammalian subject, typically by intravenous administration. However, intramuscular, subcutaneous, intraperitoneal, and other delivery routes are within the contemplation of the invention. Further, the oil-in-water emulsions of the present invention may be administered by other routes, such as oral.

Anticipated dose levels are 20 to 150 mgI/kg body weight. In the radioiodinated embodiments reported herein, specific activity for the radioactive forms ranges from about 16 to 20 μCi/ml.

In a method of use aspect of the invention, delivery of agents to the intracellular space of specific cell types within tissues could provide probes for assessment of the metabolic and/or biochemical activity of the tissue. An example of such an application of the invention is the intracellular delivery of metabolically active diagnostic imaging agents. Comparisons between clearance rates of an intracellular agent and image enhancement in normal and disease conditions could provide information about the physiological state of the tissue. If a compound that requires, for example, enzymatic hydrolysis for clearance from the tissue were selected as the agent to be delivered to the tissue, the compound would be cleared less effectively under specific disease conditions that decrease the levels or activities of the specific metabolic enzymes. Suppressed enzyme concentrations and/or activities are associated with many hepatic diseases so that the intracellular delivery of compounds in accordance with the present invention could provide a powerful means of assessing metabolic function in liver tissue.

It is further contemplated that additional target specificity may be gained by adding apolipoproteins or peptides incorporating the relevant recognition and targeting portions of the apolipoproteins into the amphipathic monolayer of the particle. The addition of steryl esters to the core of the particle, for example, might also influence the targeting of the vehicle to specific tissues by mimicking other lipoprotein classes, including, but not limited to, LDL or HDL.

While the invention has been presented in terms of a hepatocyte-selective delivery vehicle, it is possible to apply the principles of the invention to the production of tissue-specific delivery vehicles for other tissues, such as the spleen, adrenals, prostate, ovaries, lymph nodes, etc. Tissue-specific targeting compounds exploit existing cellular uptake pathways which are unique to each tissue type in an analogous manner to the exploitation of the lipid metabolism of liver tissue using the chylomicron remnant receptors on hepatocytes.

Further it should be noted that the animal models selected and used in the studies presented hereinabove, specifically rats and dogs, are well known to have hepatic physiologies that closely resemble the hepatic physiology of humans.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and description in this disclosure are proffered to facilitate comprehension of the invention, and should not be construed to limit the scope thereof.

What is claimed is:

1. A heat stable hepatocyte-selective oil-in-water emulsion comprising:
   a) between 10% and 20% (w/v) a pharmacologically inert triglyceride and a polyhalogenated triglyceride wherein the molar ratio of pharmacologically inert triglyceride to polyiodinated triglyceride is in the range of 0.3–3.0 to 1;
   b) about 2.4% (w/v) dioleoylphosphatidylcholine;
   c) up to 5% (w/v) cholesterol, wherein the molar ratio of cholesterol to dioleoylphosphatidylcholine is in the range of 0.05 to 0.70;
   d) 5% (w/v) glycerol;
   e) 0.1% α-tocopherol; and
   f) the remainder of the emulsion being water, the emulsion having a mean particle diameter of the oil phase between 50 to 200 nm with greater than 98% of the particles being less than 300 nm.

2. The heat stable hepatocyte-selective oil-in-water emulsion of claim 1 wherein the molar ratio of pharmacologically inert triglyceride and polyhalogenated triglyceride is 1:1.

3. The heat stable hepatocyte-selective oil-in-water emulsion of claim 1 wherein the amount of cholesterol is in the range of 0.4 to 0.5% (w/v).

4. The heat stable hepatocyte-selective oil-in-water emulsion of claim 1 wherein the molar ratio of cholesterol to dioleoylphosphatidylcholine is 0.4.

5. The heat stable hepatocyte-selective oil-in-water emulsion of claim 1 wherein the polyhalogenated triglyceride is a lipophilic diagnostic agent selected from the group consisting of iodinated arylaliphatic triglyceride analogs having a 1,3-disubstituted triglyceride backbone with a 3-substituted 2,4,6-triiodophenyl aliphatic chain or a monoiodophenyl aliphatic chain.

6. The heat stable hepatocyte-selective oil-in-water emulsion of claim 5 wherein the polyhalogenated triglyceride is 2-oleoylglycerol-1,3-bis[7-(3-amino-2,4,6-triiodophenyl)heptanoate].

7. The heat stable hepatocyte-selective oil-in-water emulsion of claim 6 wherein the polyhalogenated triglyceride is 2-oleoylglycerol-1,3-bis[4-(3-amino-2,4,6-triiodophenyl)butanoate].

8. The heat stable hepatocyte-selective oil-in-water emulsion of claim 1 wherein the polyhalogenated triglyceride is a 1,2,3-trisubstituted triglyceride backbone with a 3-substituted 2,4,6-triiodophenyl saturated or unsaturated aliphatic chain or a monoiodophenyl aliphatic chain.

9. The heat stable hepatocyte-selective oil-in-water emulsion of claim 1 wherein the polyhalogenated triglyceride is a fluorinated triglyceride.

10. The heat stable hepatocyte-selective oil-in-water emulsion of claim 9 wherein the fluorinated triglyceride is glyceryl-2-oleoyl-1,3-bis(trifluoromethyl)phenyl acetate.

11. The heat stable hepatocyte-selective oil-in-water emulsion of claim 9 wherein the fluorinated triglyceride is glyceryl-2-oleoyl-1,3-bis(3,5-bis-hexafluoroisopropyl)phenyl heptanoate.

12. A method of computerized tomographic imaging comprising the steps of:
   a) administering an imaging amount of the oil-in-water emulsion of claim 1 to a mammal wherein the oil-in-water emulsion contains a computerized tomography imaging agent; and
   b) when the imaging amount of the oil-in-water emulsion has reached the site to be imaged, carrying out computerized tomographic imaging of the site.

13. A heat stable oil-in-water emulsion comprising:
   a) up to 50% (w/v) of a lipophilic diagnostic agent selected from the group consisting of iodinated arylaliphatic triglyceride analogs having a 1,3-disubstituted triglyceride backbone with a 3-substituted 2,4,6-triiodophenyl aliphatic chain or a monoiodophenyl aliphatic chain;
   b) up to 10% (w/v) phospholipid emulsifier;
   c) up to about 5% (w/v) cholesterol;
   d) up to 5% (w/v) of a sodium-ion free osmolality adjusting agent; and
   e) the remainder being sterile water, the emulsion having a mean particle diameter of the oil phase between 50 to 200 nm with greater than 98% of the particles being less than 300 nm, and being able to withstand heat sterilization without a significant change in mean particle size distribution and without losing its ability to associate with apoprotein E so as to be hepatocyte-selective.

14. The heat stable hepatocyte-selective oil-in-water emulsion of claim 13 wherein the iodinated arylaliphatic triglyceride is 2-oleoylglycerol-1,3-bis[7-(3-amino-2,4,6-triiodophenyl)heptanoate].

15. The heat stable hepatocyte-selective oil-in-water emulsion of claim 13 wherein the iodinated arylaliphatic triglyceride is 2-oleoylglycerol-1,3-bis[4-(3-amino-2,4,6-triiodophenyl)butanoate].

16. A method of computerized tomographic imaging comprising the steps of:
   a) administering an imaging amount of the oil-in-water emulsion of claim 13 to a mammal wherein the oil-in-water emulsion contains a computerized tomography imaging agent; and
   b) when the imaging amount of the oil-in-water emulsion has reached the site to be imaged, carrying out computerized tomographic imaging of the site.

17. A heat stable oil-in-water emulsion comprising:
   a) up to 50% (w/v) of a lipophilic diagnostic agent selected from the group consisting of iodinated arylaliphatic triglyceride analogs having a 1,2,3-trisubstituted triglyceride backbone with a 3-substituted 2,4,6-triiodophenyl aliphatic chain or a monoiodophenyl aliphatic chain;
   b) up to 10% (w/v) phospholipid emulsifier,
   c) up to about 5% (w/v) cholesterol;
   d) up to 5% (w/v) of a sodium-ion free osmolality adjusting agent; and
   e) the remainder being sterile water, the emulsion having a mean particle diameter of the oil phase between 50 to 200 nm with greater than 98% of the particles being less than 300 nm, and being able to withstand heat sterilization without a significant change in mean particle size distribution and without losing its ability to associated with apoprotein E so as to be hepatocyte-selective.

18. A method of computerized tomographic imaging comprising the steps of
   a) administering an imaging amount of the oil-in-water emulsion of claim 17 to a mammal wherein the oil-in-water emulsion contains a computerized tomography imaging agent; and
   b) when the imaging amount of the oil-in-water emulsion has reached the site to be imaged, carrying out computerized tomographic imaging of the site.

* * * * *